(12) United States Patent
Xu

(10) Patent No.: US 11,617,369 B2
(45) Date of Patent: Apr. 4, 2023

(54) ANTIMICROBIAL GALLIUM COMPOUNDS AND METHODS

(71) Applicant: The Board of Supervisors of Louisiana State University and Agricultural and Mechanical College, Baton Rouge, LA (US)

(72) Inventor: Xiaoming Xu, Kenner, LA (US)

(73) Assignee: THE BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 75 days.

(21) Appl. No.: 17/003,765

(22) Filed: Aug. 26, 2020

(65) Prior Publication Data

US 2020/0390104 A1 Dec. 17, 2020

Related U.S. Application Data

(63) Continuation-in-part of application No. PCT/US2019/019578, filed on Feb. 26, 2019.

(60) Provisional application No. 62/635,243, filed on Feb. 26, 2018.

(51) Int. Cl.
| | |
|---|---|
| *A01N 59/16* | (2006.01) |
| *A61K 6/20* | (2020.01) |
| *A61K 6/84* | (2020.01) |
| *A01N 59/10* | (2006.01) |
| *A61K 8/19* | (2006.01) |

(52) U.S. Cl.
CPC .............. *A01N 59/16* (2013.01); *A01N 59/10* (2013.01); *A61K 6/20* (2020.01); *A61K 6/84* (2020.01); *A61K 8/19* (2013.01)

(58) Field of Classification Search
CPC ........ A01N 59/16; A01N 59/10; A01N 25/34; A01N 55/02; A01N 37/36; A01N 37/44; A61K 6/20; A61K 6/84; A61K 8/19; A61Q 11/00; C01G 15/006
See application file for complete search history.

(56) References Cited

U.S. PATENT DOCUMENTS

| | | | |
|---|---|---|---|
| 3,532,787 A | 10/1970 | Muhler | |
| 2005/0013836 A1* | 1/2005 | Raad ...................... | A01N 43/54 514/35 |
| 2006/0018945 A1 | 1/2006 | Britigan et al. | |
| 2013/0302427 A1 | 11/2013 | Arvidsson et al. | |
| 2014/0017637 A1 | 1/2014 | Cinader, Jr. et al. | |
| 2014/0193520 A1* | 7/2014 | Perl ........................ | A23K 20/20 424/650 |

FOREIGN PATENT DOCUMENTS

| | | | | |
|---|---|---|---|---|
| EP | 2830673 | | 2/2015 | |
| WO | WO-2008100907 A2 * | 8/2008 | ........... | C07C 233/49 |
| WO | WO-2014168912 A1 * | 10/2014 | ........... | A61K 6/0047 |
| WO | 2016/194692 | | 12/2016 | |
| WO | 2019/165425 | | 8/2019 | |

OTHER PUBLICATIONS

Cochis et al. "Data in support of Gallium (Ga3+) antibacterial activities to counteract *E.coli* and *S. epidermidis* biofilm formation onto pro-osteointegrative titanium surfaces" Data in Brief. Jan. 22, 2016 (Jan. 22, 2016) vol. 6, p. 758-762; entire document.

Cochis, A., et al. "The effect of silver or gallium doped titanium against the multidrug resistant Acinetobacter baumannii." Biomaterials 80 (2016): 80-95.

International Search Report for PCT/US2019/019578.

Kenawy E-R et al., The Chemistry and Applications of Antimicrobial Polymers: a State-of-the-Art Review. Biomacromolecules 2007; 8(5):1359-1384.

Minandri, Fabrizia, et al. "Promises and failures of gallium as an antibacterial agent." Future microbiology 9.3 (2014): 379-397.

Rzhepishevska et al. "The Antibacterial Activity of Ga3+ Is Influenced by Ligand Complexation as Well as the Bacterial Carbon Source" Antimicrobial Agents and Chemotherapy. Dec. 2011, vol. 55, p. 5568-5580; p. 5569, left col. para 4, 6, p. 5579, left col. para 2.

Sahdev, Rohan, et al. "Potential use of gallium-doped phosphate-based glass material for periodontitis treatment." Journal of Biomaterials Applications 30.1 (2015): 85-92.

Valappil, S. P., et al. "Effect of gallium on growth of *Streptococcus mutans* NCTC 10449 and dental tissues." Caries research 48.2 (2014): 137-146.

Wang, Yapin, et al. "Synthesis and characterization of new antibacterial fluoride-releasing monomer and dental composite." ACS macro letters 2.1 (2013): 59-62.

Written Opinion for PCT/US2019/019578.

\* cited by examiner

*Primary Examiner* — Adam C Milligan
*Assistant Examiner* — Amanda Michelle Petritsch
(74) *Attorney, Agent, or Firm* — Baker Donelson

(57) ABSTRACT

This invention relates to antimicrobial gallium compounds, and to monomers containing gallium complex moieties that can be used in oral care products and dental materials, and which can reduce or eliminate dental caries and bacterial or fungal infections associated with medical and dental devices.

18 Claims, 18 Drawing Sheets
(16 of 18 Drawing Sheet(s) Filed in Color)

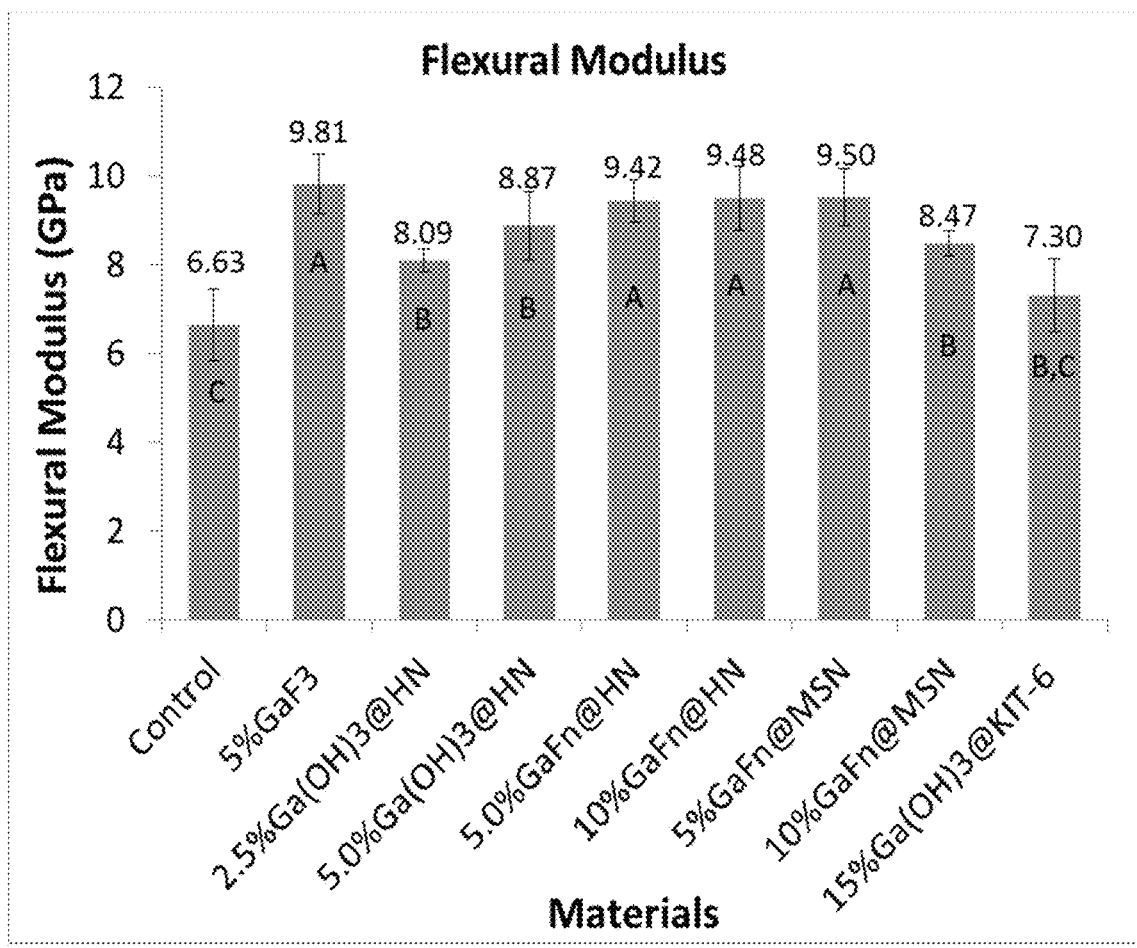
FIG. 2 CON'T

GaFn@MSN (ACS Materials)     GaFn@MSN (advanced materials)

GaFn@SBA-15 (synthesized)     GaFn@KIT-6 (ACS Materials)

| Materials | Control | Experimental | | | | | |
|---|---|---|---|---|---|---|---|
| Monomers | BisGMA/ EPBADMA /HDDMA (4:4:2) 29 wt% | Same as control | | | | | |
| | No Ga compound | 5%GaF$_n$ @HN | 10%GaF$_n$ @HN | 5%GaF$_n$ @MSN | 10%GaF$_n$ @MSN | 5%GaF$_n$ @SBA-15 | 10%GaF$_n$ @SBA-15 | 15%Ga(OH)$_3$ @KIT-6 |
| Filler | Silanized F-releasing glass filler (Caulk/Dentsply) 70 wt% | 65% | 60% | 65% | 60% | 65% | 60% | 55% |
| Photo-initiator | CQ/4E/PO (2:4:4) 1 wt% | Same as control | | | | | |

*FIG. 7*

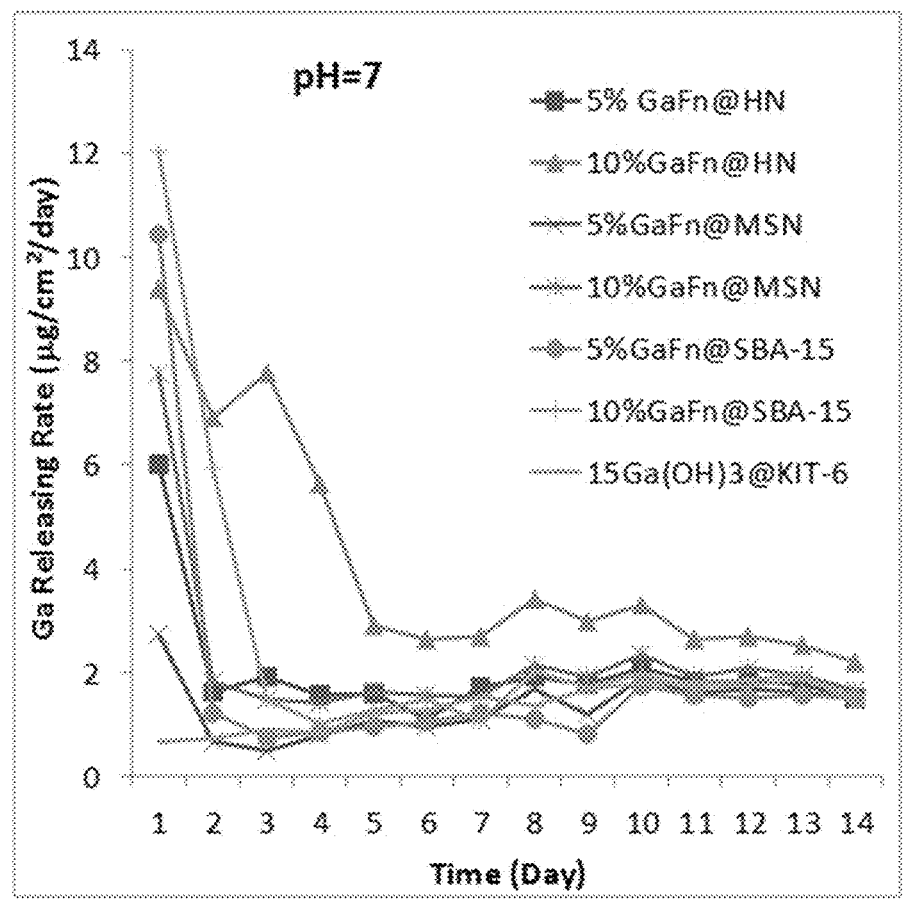
*FIG. 9 CON'T*

ANTIMICROBIAL GALLIUM COMPOUNDS AND METHODS

This application is a continuation-in-part of PCT/US2019/019578, filed on Feb. 26, 2019, which claims priority from U.S. Provisional Patent Application No. 62/635,243, filed on Feb. 26, 2018, the entire contents of each of which are incorporated herein by reference in its entirety.

GOVERNMENT INTERESTS

This invention was made with government support under Grant No. R01DE026782 awarded by the National Institutes of Health. The government has certain rights in the invention.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

This invention relates to antimicrobial gallium compounds, and to monomers containing gallium complex moieties that can be used in oral care products and dental materials, and which can reduce or eliminate dental caries and bacterial or fungal infections associated with medical and dental devices.

BACKGROUND

Biomaterials can be defined as any matter, surface, or construct that interacts with a biological system. Biomaterials can be used in manufacturing of medical devices and dental devices, all of which tend to suffer a common problem of device-related infection. For example, one of the most common device-related infections occurs with dental devices, specifically infections associated with use of biomaterials to treat dental caries.

SUMMARY OF THE INVENTION

The present invention provides an antimicrobial composition comprising a chemical compound having the following formula:

$$M_m L_L GaX_n. \quad \text{Formula (1)}$$

The present invention further provides an antimicrobial composition comprising a chemical compound having the following formula:

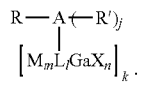

Formula (2)

In embodiments of Formula (1) and/or (2), M is a positive ion, for example hydrogen, sodium, potassium, ammonium, or a quaternary ammonium.

In embodiments of Formula (1) and/or (2), L is a chelating ligand.

In embodiments of Formula (1) and/or (2), X is an anion, for example hydroxide, nitrate, chloride, and fluoride.

In embodiments of Formula (1) and/or (2), j is an integer from 0 to 4.

In embodiments of Formula (1) and/or (2), l is an integer number from 1 to 3.

In embodiments of Formula (1) and/or (2), m is an integer number from 0 to 6.

In embodiments of Formula (1) and/or (2), n is an integer number from 0 to 6.

In embodiments of Formula (1) and/or (2), k is an integer number from 1 to 3.

In embodiments of Formula (2), R is a substituted or unsubstituted aliphatic or aromatic group having 2 to 50 carbon atoms. Embodiments can also have at least one polymerizable group. For example, in embodiments of Formula (2), R is substituted or unsubstituted aliphatic or aromatic group having 2 to 50 carbon atoms, and having at least one polymerizable group.

In embodiments of Formula (2), R' is a substituted or unsubstituted aliphatic or aromatic group having 2 to 50 carbon atoms, and having at least one polymerizable group.

In embodiments of Formula (2), A is a substituted or unsubstituted aliphatic or aromatic linkage group having 0 to 100 carbon atoms.

In embodiments of a compound of Formula (1), L comprises one of following chelating ligands: oxalic acid, citric acid, phthalic acid, glutamic acid, tyrosine, serine, iminodiacetic acid, ethylenediiminodiacetic acid, nitrilotriacetic acid, catechol, acetylacetone, hexafluoroacetylacetone, benzoylacetone, N-(2-hydroxybenzyl)iminodiacetic acid, N-(2-hydroxyethyl)iminodiacetic acid, N-(2-aminoethyl)iminodiacetic acid, ethylendinitrilotetraacetic acid, diglycylethylenediaminetetraacetic acid, diethylenetrinitrilopentaacetic acid, salicylic acid, ethylenediiminodiacetic acid (EDDA), N,N-bis(carboxymethyl)aminoacetohydroxamic acid, ethylenediiminobis[(2-hydroxyphenyl)acetic acid] (EHPG), and diethylenetrinitrilopentaacetic acid (DTPA).

In embodiments of a compound of formula (2), L comprises one of the following chelating group (L2-L22) with dotted line the indicating bonding location:

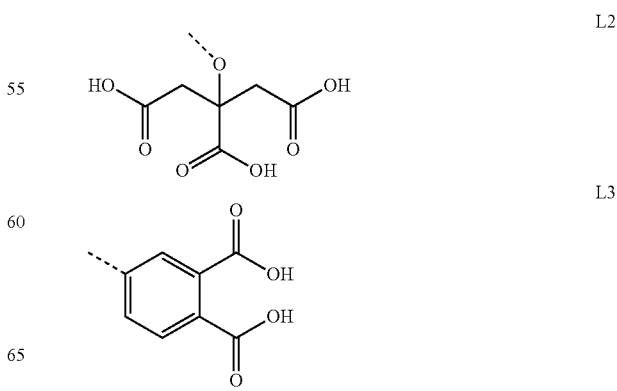

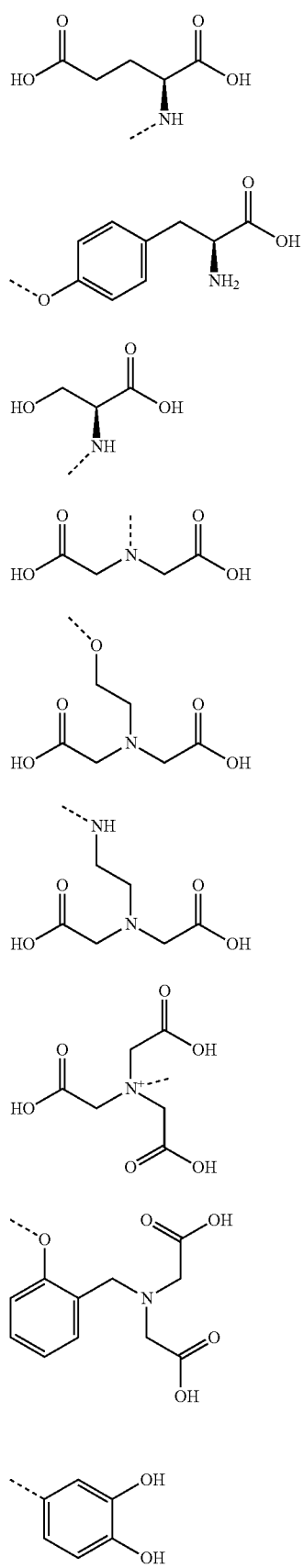
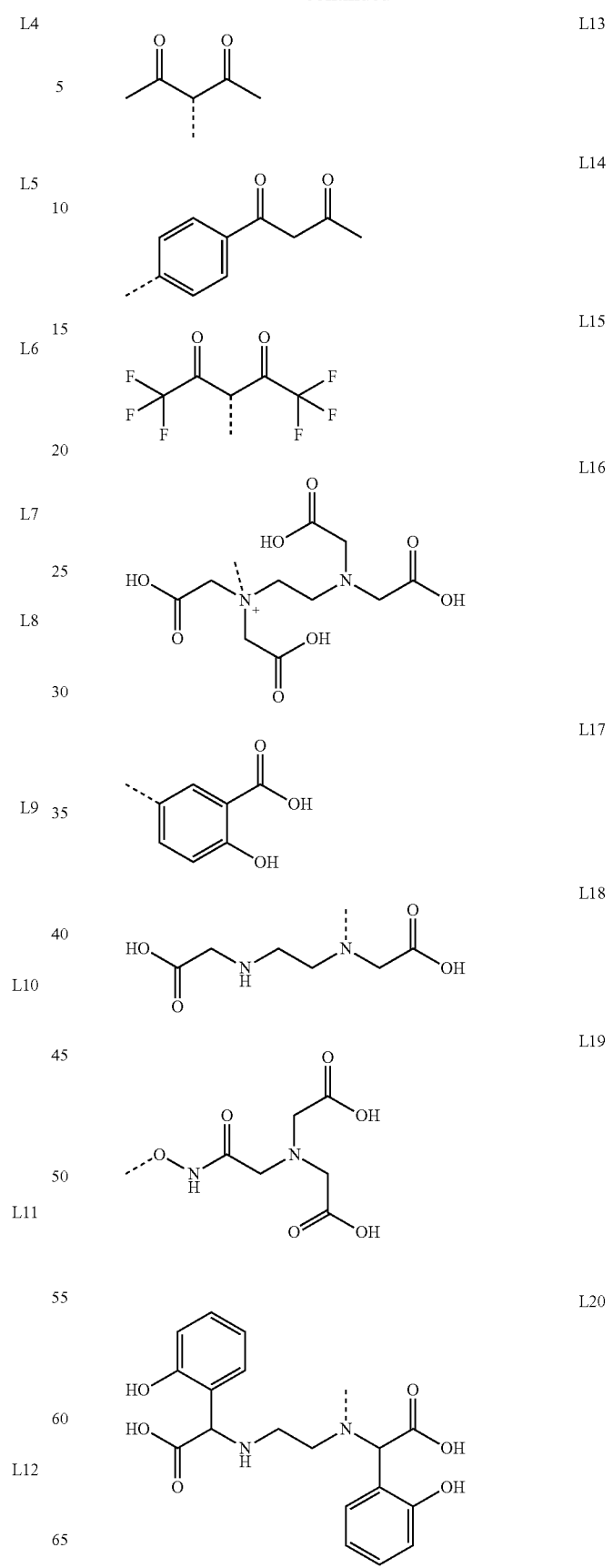

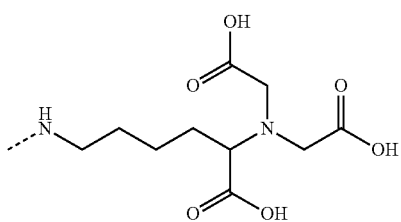
L22

In embodiments of the invention, R and R' are one of R1-R6:

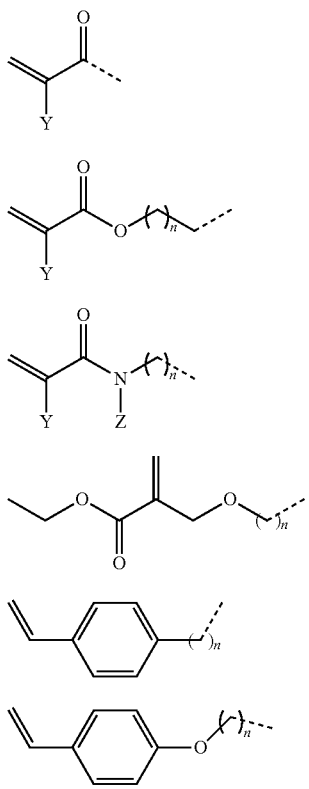

wherein Y is selected from the group consisting of hydrogen, and an unsubstituted aliphatic group containing 1 to 6 carbons;
wherein Z is selected from the group consisting of hydrogen, and an unsubstituted aliphatic group containing 1 to 6 carbons;
wherein n is a positive integer from 0 to 20.

In embodiments of the invention, A is one of A1-A11:

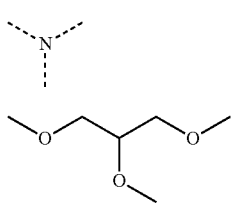
A1
A2

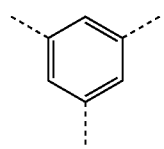
A3

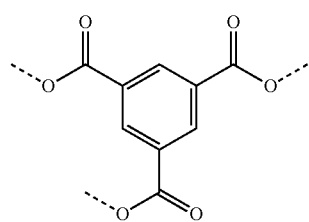
A4

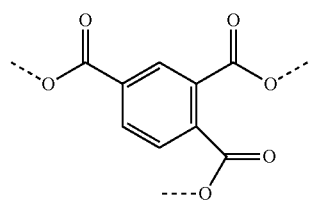
A5

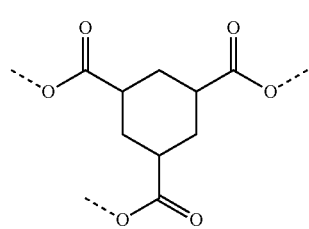
A6

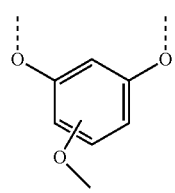
A7

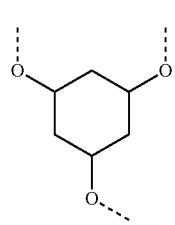
A8

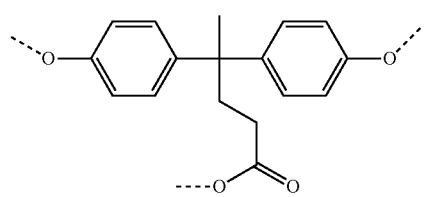
A9

A10

-continued

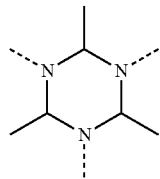

A11

In embodiments of the invention, Y is a methyl group and Z is hydrogen.

In embodiments of the invention, Y is hydrogen and Z is selected from the group consisting of of methyl and ethyl group.

In embodiments of the invention, X is fluoride ion.

In embodiments of the invention, R and R' are the same.

Embodiments further comprise the polymerized form of the compound in Formulas (2).

Embodiments further comprise a polymer comprising a compound of Formula (1).

Embodiments further comprise a dental composite containing 0.5% to 15% of antimicrobial gallium compound having formulas (1) as the filler and 0.5% to 15% of antimicrobial gallium monomer having formulas (2), such as described herein, or its cured polymer.

Embodiments further comprise a denture base material containing 0.5% to 15% of antimicrobial compound having formulas (1) or formulas (2), or both, or its cured polymer.

Embodiments further comprise a dental bonding agent containing 0.5% to 15% of antimicrobial compound having formulas (1) or formulas (2), or both.

Embodiments further comprise a dental sealant containing 0.5% to 15% of antimicrobial compound having formulas (1) or formulas (2), or both.

Embodiments further comprise a dental resin cement containing 0.5% to 15% of antimicrobial compound having formulas (1) or formulas (2), or both.

Embodiments further comprise a glass ionomer containing 0.1% to 20% of antimicrobial compound having formulas (1) or formulas (2) or both.

Embodiments further comprise a resin-modified glass ionomer containing 0.1% to 20% of antimicrobial compound having formulas (1) or formulas (2) or both.

Embodiments further comprise a tooth paste containing 0.1% to 5% of antimicrobial compound having formulas (1).

Embodiments further comprise a topic agent containing 0.1% to 10% of antimicrobial compound having formulas (1).

Embodiments further comprise a dental varnish containing 0.1% to 10% of antimicrobial compound having formulas (1) or formulas (2), or both.

Embodiments further comprise a mouth rinse containing 0.01% to 5% of antimicrobial compound having formulas (1).

Embodiments further comprise a mouth guard containing 0.1% to 10% of antimicrobial compound having formulas (1) or formulas (2), or both.

Embodiments further comprise a medical device containing 0.1% to 20% of antimicrobial compound having formulas (1) or formulas (2), or both.

Embodiments further comprise a method of preparing antibacterial dental composite. For example, the method comprises the following steps:

a) preparation of nanoparticles containing the gallium compounds as described herein, such as by dissolving the gallium compound formulas (1) in methanol or ethanol or aqueous methanol or ethanol containing up to 50% water to 2M or saturation concentration; adding 20% w/v mesoporous silica nanoparticles or halloysite clay nanotube, stirring for 10 min and degassing under reduced pressure (20 mmHg) for 10 min, and repeating the stirring-degassing process, such as repeating five times; filtrating the suspension and drying the particles at 70-100° C. and under vacuum overnight.

b) mixing 1%-30% w/w dried nanoparticles prepared in step (a) with 49%-80% silanized fluroalluminosilicate filler particles or other filler particles for dental composite known in the art, 49%-14% mixed dental monomers, which may include 1% to 50% (of total monomers) the monomer described herein, and 0.5%-2% chemical initiators or photoinitiators known to one skilled in the art.

In embodiments, the antibacterial composites can comprise compounds of Formulas (1) and/or Formulas (2).

Embodiments further comprise a method of preparing antibacterial fluoride-releasing glass powders for glass ionomers and resin-modified glass ionomers. These glass powders can also be used as filler in other dental materials (for example, composites, bonding agents, luting cements, sealants and orthodontic adhesives). In embodiments, the method comprises the following steps:

a) Mixing the following ingredients (wt %) in a ceramic or platinum crucible: $SiO_2$, 29%, $CaF_2$ 34%, $AlPO_4$ 9.9%, $Al_2O_3$ 5-11%, $Ga_2O_3$ 5-11%, $AlF_3$ 0-5%, $GaF_3$ 0-5%, $Na_3AlF_6$ 0-5%, $Na_3GaF_6$ 0-5%, and $SrO_2$ or $BaO_2$. 0.1%.

b) Heating the above mixture in a furnace or oven until the mixture is completely melted, such as at or above 1200-1600° C.

c) Quenching the molten glass by quickly pouring it into deionized water.

d) Collecting the cooled glass, drying and grinding it into powder (such as particle size: 0.01-50 micrometer). This step can be performed using a ball mill machine or pneumatic milling machine.

In embodiments, antibacterial fluoride-releasing glass powers, such as those for glass ionomers and resin-modified glass ionomers, can comprise compounds of Formulas (1) and/or Formulas (2).

Embodiments further comprise a method of preparing antibacterial gallium-releasing glass ionomer, wherein the above gallium-releasing and fluoride-releasing glass powder reacts with the polyalkenic acids known in the prior art.

In embodiments, antibacterial gallium-releasing glass ionomers can comprise compounds of Formulas (1) and/or Formulas (2).

Embodiments further comprise a method of preparing antibacterial gallium-releasing resin-modified glass ionomer, wherein the above gallium-releasing and fluoride-releasing glass powder reacts with the liquid that is the aqueous solution of resin-modified polyalkenic acids known by one skilled in the art.

In embodiments, antibacterial gallium-releasing resin-modified glass ionomers can comprise compounds of Formulas (1) and/or Formulas (2).

Other objects and advantages of this invention will become readily apparent from the ensuing description.

BRIEF DESCRIPTION OF THE FIGURES

This patent or application file contains at least one drawing executed in color. Copies of this patent or patent application publication with color drawing(s) will be provided by the Office upon request and payment of the necessary fee.

FIG. 7 shows compositions of experimental composites.

DETAILED DESCRIPTION OF THE INVENTION

Abbreviations and Definitions

Figure 1:
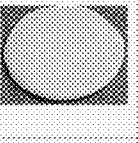
FIG. 1 shows color index of composites. Color Index Difference with the Control: $\Delta E^* = (\Delta L^{*2} + \Delta a^{*2} + \Delta b^{*2})^{1/2}$.

Detailed descriptions of one or more preferred embodiments are provided herein. It is to be understood, however, that the present invention may be embodied in various forms, for example, the polymerized forms of formulas (2). Therefore, specific details disclosed herein are not to be interpreted as limiting, but rather as a basis for the claims and as a representative basis for teaching one skilled in the art to employ the present invention in any appropriate manner.

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

Gallium (III)

Dental caries, also known as tooth decay or a dental cavity, is a worldwide pandemic problem that is caused by a bacterial infection that may lead to progressive demineralization and/or destruction of hard tissues of a tooth. Worldwide, approximately 36% of the population (2.43 billion people) have dental caries in their permanent teeth. In the United States, dental caries is the most common chronic childhood disease, being at least five times more common than asthma, and is a primary pathological cause of tooth loss in children. Dental caries do not only affect children in the US, as upwards of 60% of adults over the age of fifty experience caries. If left untreated, dental caries can lead to pain, tooth loss, and further oral infection. For large lesions, progressive decay can be treated by filing with restorative materials, such as amalgam, composite resin, porcelain and gold. Unfortunately, this filing often has to be redone due to restoration failure, and the site serves as a vulnerable site for further decay and infection.

Oral care products, for example tooth pastes, mouth rinse, topic fluoride agents, and varnishes, can prevent and reduce dental caries and periodontal disease. They can contain various amount of fluoride, ranging from 0.15 w/v % (0.079 M) fluoride in non-prescription tooth pastes, 5000 ppm (0.26 M) fluoride in prescription tooth paste, to 2.0% NaF (0.48M F$^-$) in topical fluoride agents, to 5% NaF (1.19M F$^-$) in fluoride varnishes. Although they have varied anti-cares effects, their antibacterial effect is rather limited and short-lived, particularly for the non-prescription tooth pastes that have low fluoride concentration.

Silver diamine fluoride (10-40%) is an antibacterial topical fluoride agent. It has more effective caries-set efficacy (stopping the progress of caries) than fluoride varnishes. However, it leaves an undesirable black color on the treated teeth for a long time. Therefore, it is only desirable and/or suitable for treating primary (i.e., baby) teeth in children because those primary teeth will eventually fall off and replaced by permanent teeth.

Secondary caries, also known as recurrent caries, are caries that appear at restoration margins, and are a primary cause of restoration failure. Prevention of secondary caries can be attempted through use of fluoride-releasing and/or antibacterial dental materials; however, antibacterial effects of these materials, which can contain releasable reagents (e.g., chlorhexidine), have antibacterial efficacy for only a short time (<1 week). Also, these materials often suffer from poor mechanical properties due to porosity in the materials after drug release. Dental materials containing silver salts or silver nanoparticles have shown antibacterial effects. However, such materials usually have poor (dark brown or gray) colors or shades, and therefore, are not suitable for restorations in anterior (front) teeth.

Polymers with antimicrobial activities, such as antibacterial and antifungal activities, that are known as polymeric biocides or antimicrobial polymers have drawn interest in the fields of biomedical materials and medical implants. See, for example, Kenawy E-R et al., The Chemistry and Applications of Antimicrobial Polymers: A State-of-the-Art Review. *Biomacromolecules* 2007; 8(5):1359-1384, which is incorporated by reference herein in its entirety. Biocide moieties can include, for example, quaternary ammonium, pyridinium, phosphonium, and sulfonium salts. The mechanism of action of quaternary compounds can be direct cationic binding to cell wall components, leading to disruption of the cell wall membrane, and subsequently leakage of cell contents and cell death. To achieve high antimicrobial efficacy, the quaternary salt typically has at least one long-chain alkyl or substituted alkyl group, and a relatively low tendency to form an ion-pair with a counter ion. The limitation of this type of antimicrobial polymers is that they have only surface antimicrobial (contact-kill) effect, which can be overwhelmed by the biofilms residues (debris of dead bacteria) or adsorbed proteins.

Gallium (III) compounds can have antibacterial effects against wide spectra of bacteria, fungi and viruses. Gallium (III) compounds can be employed as diagnostic and therapeutic tools in clinical medicine. Gallium is the second most used metal, after platinum, in cancer treatment. Ganite®, a citrate-buffered $Ga(NO_3)_3$ formulation was approved by the FDA for treatment of malignancy-associated hypercalcemia.

The probable antimicrobial mechanism of gallium compounds is that $Ga^{3+}$ ion is very similar to $Fe^{3+}$ ion except that $Ga^{3+}$ cannot be reduced (to $Ga^+$) under physiological conditions. Therefore, $Ga^{3+}$ can replace $Fe^{3+}$ in many Fe-containing enzymes in fast-growing bacteria and viruses and disrupt their enzymatic functionalities leading to the death of bacteria or viruses. Many life-threatening bacteria, such as *Pseudomonas aeruginosa* and *Mycobacterium tuberculosis*, are highly susceptible to Ga(III) compounds (see Minandri F, et al., Promises and failures of gallium as an antibacterial agent. Future Microbiology 2014, 9(3): 379-397, which is incorporated by reference here in its entirety). Gallium-incorporated phosphate-based glasses can inhibit the growth of *Porphyromonas gingivalis* biofilm and matrix metalloproteinase-13 without any toxic effect on animal (rat) (see Sahdev R, et al., Potential use of gallium-doped phosphate-based glass material for periodontitis treatment, J Biomater Appl 2015, 30(1) 85-92, which is incorporated by reference herein in its entirety).

Gallium ions can also inhibit other MMPs, which degrade collagen fibrils, since gallium ions form a stable complex with cysteine on the MMPs thus it can block the active site of the MMPs. Coating of Ti with Ga-L-cysteine has shown the better antibacterial effect against multidrug-resistant *Acinetobacter baumannii* than Ag-L-cysteine or nAg (see Cochis A, et al., The effect of silver or gallium doped titanium against the multidrug resistant *Acinetobacter baumannii*. Biomaterials, 2016, 80, 80-95, which is incorporated by reference herein in its entirety). Gallium compounds in the form of bioglass can also reduce *S. mutans* biofilm without adverse effect on dentin and enamel (see Valappil S P, et al., Effect of Gallium on Growth of *Streptococcus mutans* NCTC 10449 and Dental Tissues. Caries Res, 2014; 48:137-146, which is incorporated by reference herein in its entirety).

European patent application EP2830673 A1 shows the application of gallium oxide $Ga_2O_3$ as a surface coating on the substrates of dental and medical devices (which is incorporated by reference in its entirety). The substrates include metal, ceramic and composites. US patent application (US 2013/0302427 A1; which is incorporated by reference in its entirety) shows the use of nanoparticles of gallium and bismus compounds coated on different substrates (metal and ceramics) and medical devices. The gallium compounds include, but are not limited to, gallium oxide, gallium nitride, metal oxides comprising gallium and metal nitrides comprising gallium.

The most widely used gallium compound is $Ga(NO_3)_3$ but gallium(III) forms various hydroxyl complexes in aqueous medium and their compositions depend on pH values. For example, at pH<1 gallium is present almost completely as $Ga^{3+}$ ions, the maximum of the $Ga(OH)^{2+}$ fraction is at pH-3, the maximum of the $[Ga(OH)_2]^+$ fraction is at pH-4, whereas at pH=7 gallium is almost completely as hydrated $Ga(OH)_3$, which is a white solid with low solubility in water (Ksp=$[Ga^{3+}][OH^-]^3$=3.28×10$^{-36}$). The crystalline gallium oxide $Ga_2O_3$ is insoluble in water. Therefore, to increase the solubility and bioavailability of gallium at or near neutral (pH=7) conditions, the formation of soluble coordination compounds (complexes) of gallium with different ligands is necessary.

Gallium (III) fluoride or gallium trifluoride ($GaF_3$) is a white solid that is sparingly soluble in water (0.002 g/L, 1.58×10$^{-5}$M). Gallium (III) also forms a series of fluoride complex ions $[GaF_n]^{3-n}$ (n=1-6). When n>3, the solubility of gallium fluoride complexes is increased with increase of fluoride concentration. The solubility of gallium fluoride complexes is also pH dependent. Therefore, without being bound by theory, there is an application of gallium fluoride complexes in oral health products that contain high concentration of fluoride.

Gallium (III) can form water soluble complexes (coordination compounds) with a wide variety of chelating ligands that have two or more ligands. Non-limiting examples of chelating ligands include oxalic acid, citric acid, phthalic acid, glutamic acid, tyrosine, serine, iminodiacetic acid, ethylenediiminodiacetic acid, nitrilotriacetic acid, catechol, acetylacetone, hexafluoroacetylacetone, benzoylacetone, N-(2-hydroxybenzyl)iminodiacetic acid, N-(2-hydroxyethyl)iminodiacetic acid, N-(2-aminoethyl)iminodiacetic acid, ethylendinitrilotetraacetic acid, diglycylethylenediaminetetraacetic acid, diethylenetrinitrilopentaacetic acid, and salicylic acid.

Gallium compounds have not been used as filler particles in resin-based dental materials. For example, there is no report on the use of gallium compounds in glass ionomer (cement) or resin-modified glass ionomer (cement). There is also no report on the use of gallium compounds in oral care products, non-limiting examples of which comprise tooth pastes, topic agents, varnishes, and mouth rinse.

Gallium (III) Compositions

Embodiments as described herein comprise the designing and applications of gallium compounds (for example gallium fluorides, chloride, hydroxides, and complexes with chelating dental monomers), and the use of mesoporous silica nanoparticles (MSN) and halloysite nanotube (HN) for controlled release of these gallium compounds from dental materials. MSN and HN loaded with gallium compounds can also be dispersed more uniformly in dental monomers than the gallium compounds themselves, can minimize the porosity (voids) in the materials after the release of the compounds, and maintain the material integrity and mechanical properties. Such materials can be used as components of dental materials, reducing secondary caries, and prolonging the service life of dental restorations, or can be used in other medical materials and devices.

As described herein, embodiments can provide medical and dental materials with antibacterial activity without deteriorating their physical properties (e.g., color and color stability). For example, unlike the dental materials containing sliver salts or silver nanoparticles that usually show dark brown or grey shade even at very low concentration (0.05%), gallium compounds are white or colorless. Therefore, dental materials, such as those containing as high concentration as 15%, show essentially the same color shade as the control.

Further, the dental materials containing gallium-loaded MSN or HN can release gallium ions and compounds in a controlled manner for an extended period of time and in response to the acidity (pH value) of the oral environment. At the same time they can maintain or even increase the mechanical properties of the materials.

Still further, the chelating dental monomer can form ternary gallium fluoride complexes, which can promote the release of both gallium and fluoride via ion-exchange mechanism, enhancing caries-inhibitory effect while maintaining the material integrity and mechanical properties.

Embodiments of the present invention provide formulas of gallium compounds and novel antimicrobial monomers and polymers. Embodiments can be utilized to prevent or reduce microbial infections, such as bacterial infections or fungal infections. Such infections can include those associated with medical and/or dental devices, and biofilms accumulated on the surface of restoration or at the restoration margins.

In embodiments, such as in resin-based dental materials, an important advantage of gallium compounds, such as over silver salts or silver nanoparticle, is that the gallium compounds are white or colorless. This feature not only gives dental materials desirable aesthetics, but also allows higher amount to be used, which may lead to higher antibacterial efficacy.

An embodiment of the present invention can include dental materials (such as composites, adhesives, sealants, resin cements, glass ionomers, resin-modified glass ionomers) containing filler particles consisting of sparingly soluble gallium (hydrous)oxides or gallium (tri)fluoride, which have higher solubility than gallium oxide. These particles can provide pH-responsive controlled release of antibacterial gallium ions. The filler particles can be, for example, glass.

Glass ionomer (GI) or glass ionomer cement (GIC) is a term for glass-polyalkenoate cements and is a type of dental materials used as filling material in non-load-bearing areas, luting cement, pit-and-fissure sealant, or orthodontic bracket adhesive, for example. The setting of glass ionomers is based on the acid-base reaction between the (calciumaluminofluorosilicate) glass powder and the aqueous solution (liquid) of polyalkenic acids, which are the mixture of polymers or copolymer of acrylic acid, itaconic acid, maleic acid, tricaballic acid, and tartaric acid. The advantages of glass ionomers are: (1) they can chemically bond to tooth tissue (dentin and enamel); (2) they have good biocompatibility; and (3) they release a high amount of fluoride that can reduce secondary caries. The drawback of glass ionomers is that they are brittle and have low strength and translucency.

Resin-modified glass ionomer (RMGI) is a significant development of glass ionomer through the modification of polyalkenic acids by grafting pendent methacrylate moieties onto them or mixing with methacrylate dental monomers, and the addition of photoinitiators. RMGI has better mechanical properties and translucency than GI while releasing a similar amount of fluoride. Therefore, RMGI has wider dental applications than GI.

The glass powder used in GI and RMGI is usually comprised of a various amount of silica ($SiO_2$), alumina ($Al_2O_3$), aluminum fluoride ($AlF_3$), calcium fluoride ($CaF_2$), cryolite ($Na_3AlF_6$), aluminum phosphate ($AlPO_4$), or a combination thereof.

In embodiments, the glass ionomer and/or the resin-modified glass ionomer can comprise compounds of Formulas (1) and/or Formulas (2).

In another embodiment of this invention, an novel antibacterial gallium-releasing and fluoride-releasing glass can be made by replacing a part or all $Al_2O_3$, $AlF_3$, $Na_3AlF_6$ with $Ga_2O_3$ or $Ga(OH)_3$, $GaF_3$, or $Na_3GaF_6$, respectively. Embodiments can, for example, comprise compounds of Formulas (1) and/or Formulas (2).

Such an antibacterial gallium-releasing and fluoride-releasing glass comprise $SiO_2$, $CaF_2$, $AlPO_4$, $Al_2O_3$, $Ga_2O_3$, $AlF_3$, $GaF_3$, $Na_3AlF_6$, $Na_3GaF_6$, and $SrO_2$ or $BaO_2$. For example, such an antibacterial gallium-releasing and fluoride-releasing glass have the following compositions (wt %): $SiO_2$, 29%, $CaF_2$ 34%, $AlPO_4$ 9.9%, $Al_2O_3$ 5%-11%, $Ga_2O_3$ 5%-11%, $AlF_3$ 0-5%, $GaF_3$ 0-5%, $Na_3AlF$ 0-5%, $Na_3GaFe$ 0-5%, and $SrO_2$ or $BaO_2$. 0.1%.

In some embodiments, the $SiO_2$ composition (wt %) comprises about 1%, about 5%, about 10%, about 15%, about 20%, about 21%, about 22%, about 23%, about 24%, about 25%, about 26%, about 27%, about 28%, about 29%, about 30%, about 31%, about 32%, about 33%, about 34%, about 35%, about 40%, about 45%, or about 50% of the glass described herein.

In some embodiments, the $CaF_2$ composition (wt %) comprises about 1%, about 5%, about 10%, about 15%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 45%, or about 50% of the glass described herein In some embodiments, the $AlPO_4$ composition (wt %) comprises about 1%, about 5%, about 6%, about 7%, about 8%, about 9%, about 9.9%, about 10%, about 11%, about 12%, about 13%, about 14%, about 15%, about 20%, about 30% of the glass described herein.

In some embodiments, the $Al_2O_3$ composition (wt %) comprises about 1%, about 2%, about 3%, about 4%, about 5%, about 6%, about 7%, about 8%, about 9%, about 10%, about 11%, about 12%, about 13%, about 14%, about 15%, about 20%, about 25% of the glass described herein.

In some embodiments, the $Ga_2O_3$ composition (wt %) comprises about 1%, about 2%, about 3%, about 4%, about 5%, about 6%, about 7%, about 8%, about 9%, about 10%, about 11%, about 12%, about 13%, about 14%, about 15%, about 20%, about 25% of the glass described herein.

In some embodiments, the $AlF_3$ composition (wt %) comprises about 0%, about 1%, about 2%, about 3%, about 4%, about 5%, about 6%, about 7%, about 8%, about 9%, about 10%, about 15%, about 20%, about 25% of the glass described herein.

In some embodiments, the $GaF_3$ composition (wt %) comprises about 0%, about 1%, about 2%, about 3%, about 4%, about 5%, about 6%, about 7%, about 8%, about 9%, about 10%, about 15%, about 20%, about 25% of the glass described herein.

In some embodiments, the $Na_3AlF_6$ composition (wt %) comprises about 0%, about 1%, about 2%, about 3%, about 4%, about 5%, about 6%, about 7%, about 8%, about 9%, about 10%, about 15%, about 20%, about 25% of the glass described herein.

In some embodiments, the $Na_3GaF_6$ composition (wt %) comprises about 0%, about 1%, about 2%, about 3%, about 4%, about 5%, about 6%, about 7%, about 8%, about 9%, about 10%, about 15%, about 20%, about 25% of the glass described herein.

In some embodiments, the $SrO_2$ composition (wt %) comprises about 0%, 0.05%, about 0.06%, about 0.07%, about 0.08%, about 0.09%, about 0.1%, about 0.2%, about 0.3%, about 0.4%, about 0.5% about 0.6%, about 0.7%, about 0.8%, about 0.9%, about 1% of the glass described herein.

In some embodiments, the $BaO_2$ composition (wt %) comprises about 0%, 0.05%, about 0.06%, about 0.07%, about 0.08%, about 0.09%, about 0.1%, about 0.2%, about 0.3%, about 0.4%, about 0.5% about 0.6%, about 0.7%, about 0.8%, about 0.9%, about 1% of the glass described herein.

The particles (powder) of such a glass can be prepared by heating the mixture of above components in a furnace or oven until the mixture is completely melted, such as at 1200-1600° C., followed by quenching (quickly pouring) the molten glass into deionized water. Then the cooled glass is collected, dried, and ground into powder (for example particle size: about 0.01-about 50 micrometer) in a ball mill machine or pneumatic milling machine.

This new gallium-releasing and fluoride-releasing glass particle (powder) can be used as a component in antibacterial fluoride-releasing dental materials (composites, glass ionomers, resin-modified glass ionomers, compomers, luting cements, sealants, bonding agents, and orthodontic adhesives). Such antibacterial fluoride-releasing dental materials can comprise compounds of Formulas (1) and/or Formulas (2).

An antibacterial gallium-releasing glass ionomer can be prepared using the above gallium-releasing and fluoride-releasing glass powder reacted with the polyalkenic acids known in the prior art. Similarly, an antibacterial gallium-releasing resin-modified glass ionomer can be prepared using the above gallium-releasing and fluoride-releasing glass powder reacted with the liquid that is the aqueous solution of resin-modified polyalkenic acids known in the prior art.

The fully reacted (pre-set) glass ionomer and resin-modified glass ionomer described above can be ground into powders, freeze-dried, silanized, and used as antibacterial fluoride-releasing fillers in dental composites, resin cements, dental bonding agents, sealants, and orthodontic adhesives.

In embodiments, the glass ionomer and/or resin-modified glass ionomer can comprise compounds of Formulas (1) and/or Formulas (2).

In another embodiment, gallium complexes, such as those described in formulas herein, can be used as filler in dental materials or oral care products:

$$M_mL_lGaX_n \quad \text{Formula (1):}$$

wherein M is a positive ion for example hydrogen, sodium, potassium, ammonium, or quaternary ammonium; L is a chelating ligand; Ga is gallium (III); and X is an anion, such as hydroxide, nitrate, chloride, and fluoride, or their mixture; for example the X is fluoride; wherein l are integer number from 1 to 3; m is an integer from 0 to 6, wherein n is an integer number from 0 to 6.

In embodiments, the L in formulas (1) is chelating ligands that can form at least two coordination bonds with gallium (III) ion. Non-limiting examples of the L groups can include one or more of the following structures L1-L21:

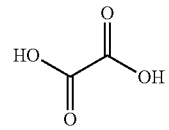

oxalic acid

L1

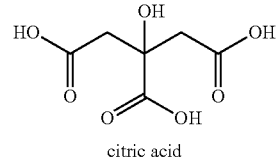

citric acid

L2

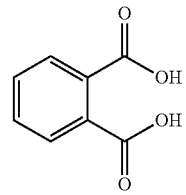

phthalic acid

L3

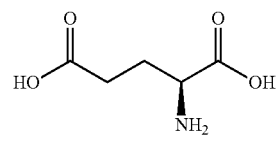

glutamic acid

L4

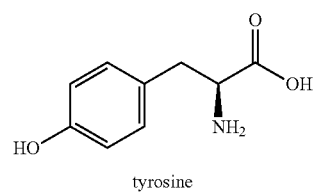

tyrosine

L5

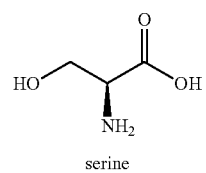

serine

L6

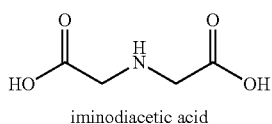
iminodiacetic acid

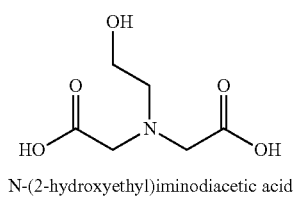
N-(2-hydroxyethyl)iminodiacetic acid

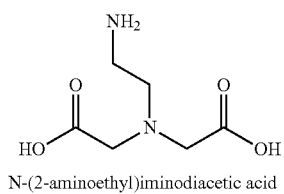
N-(2-aminoethyl)iminodiacetic acid

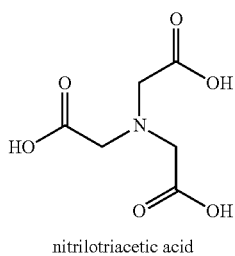
nitrilotriacetic acid

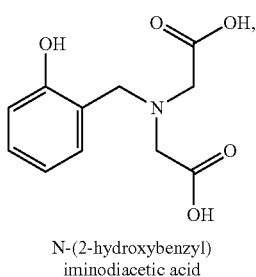
N-(2-hydroxybenzyl)iminodiacetic acid

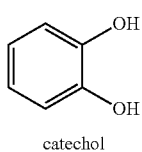
catechol

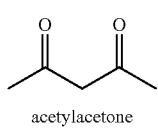
acetylacetone

benzoylacetone

L7

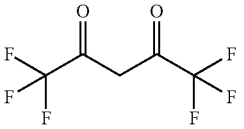
hexafluoroacetylacetone

L8

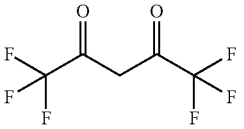
ethylendinitrilotetraacetic acid

L9

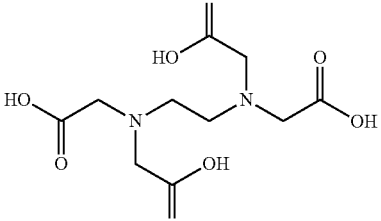
salicylic acid

L10

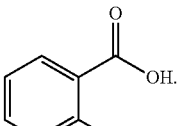
ethylenediiminodiacetic acid (EDDA)

L11

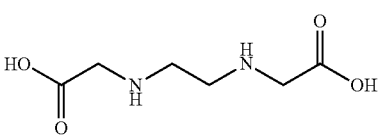
N,N-bis(carboxymethyl)aminoacetohydroxamic acid

L12

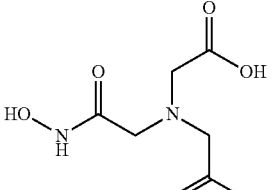
ethylenediiminobis[(2-hydroxyphenyl)acetic acid] (EHPG)

L13

L14

L15

L16

L17

L18

L19

L20

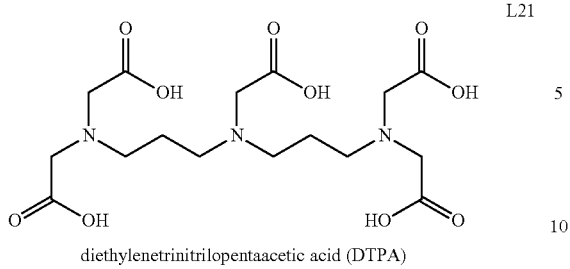

diethylenetrinitrilopentaacetic acid (DTPA)

L21

The formation of gallium chelates with the above chelating ligands, with or without additional fluoride, can ensure their solubility and stability in aqueous media or oral health products at or near neutral condition (pH 6.0-7.0). Because these chelating ligands also form stable chelates with ferric ($Fe^{3+}$) ion, the gallium complexes with these chelating ligands are more effective to disrupt bacterial Fe metabolism, and therefore, they have higher antibacterial activities than gallium nitrate and other gallium salts.

Another embodiment of this invention comprises a series of antimicrobial monomers having the following general formulas and structures:

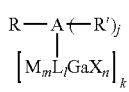

Formula (2)

wherein R and R' can be the same or different polymerizable groups selected. R can be a substituted or unsubstituted aliphatic or aromatic group, such as those having 2 to 50 carbon atoms, and having at least one polymerizable group, the polymerizable group can be located in a terminal position; A can be a substituted or unsubstituted aliphatic or aromatic linkage group, such as those having 1 to 100 carbon atoms, and at least three bonding sites; R' can be a substituted or unsubstituted aliphatic or aromatic group, such as those having 2 to 50 carbon atoms, and having at least one polymerizable group; R and R' can be the same or different; wherein at least one R or R' is present; wherein M is a positive ion of hydrogen, sodium, or potassium, ammonium, or quaternary ammonium, L is a chelating group, Ga is gallium (III), and X is a anion, such as hydroxide, nitrate, chloride, and fluoride; the preferred X is fluoride; wherein j is a integer from 0 to 4, wherein l is an integer number from 1 to 3; m is an integer number from 0 to 6, wherein n is an integer number from 0 to 6; wherein k is an integer number from 1 to 3.

Examples of the L groups in the formulas (2) include, but are not limited to, one or more of the chelating groups L2-L22 with the dotted line indicating the bonding location:

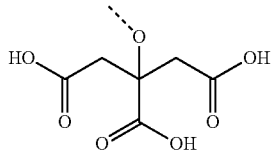

L2

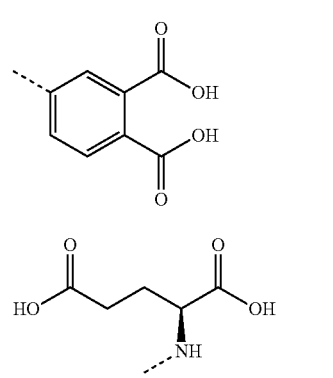

L3

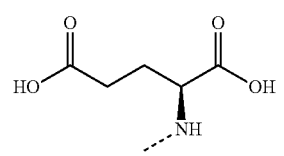

L4

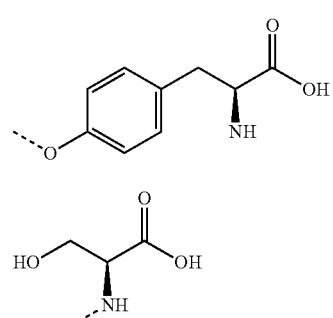

L5

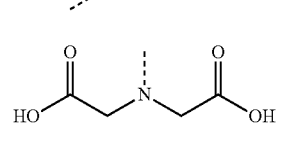

L6

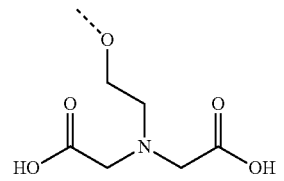

L7

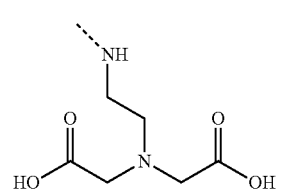

L8

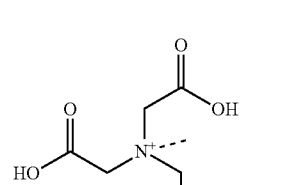

L9

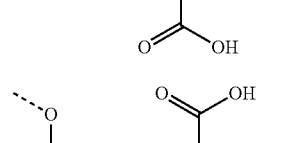

L10

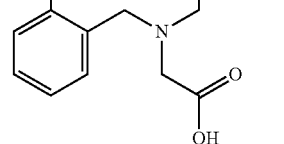

L11

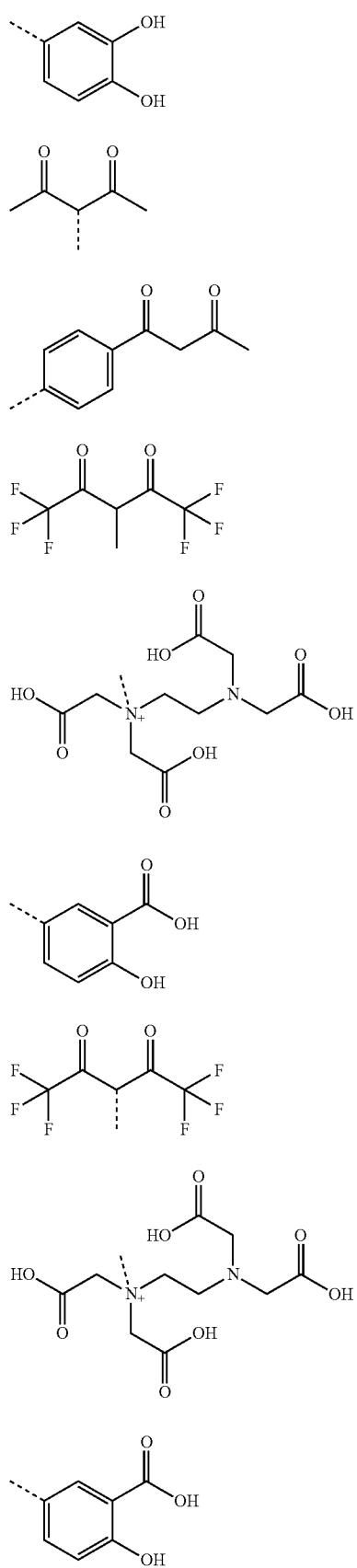

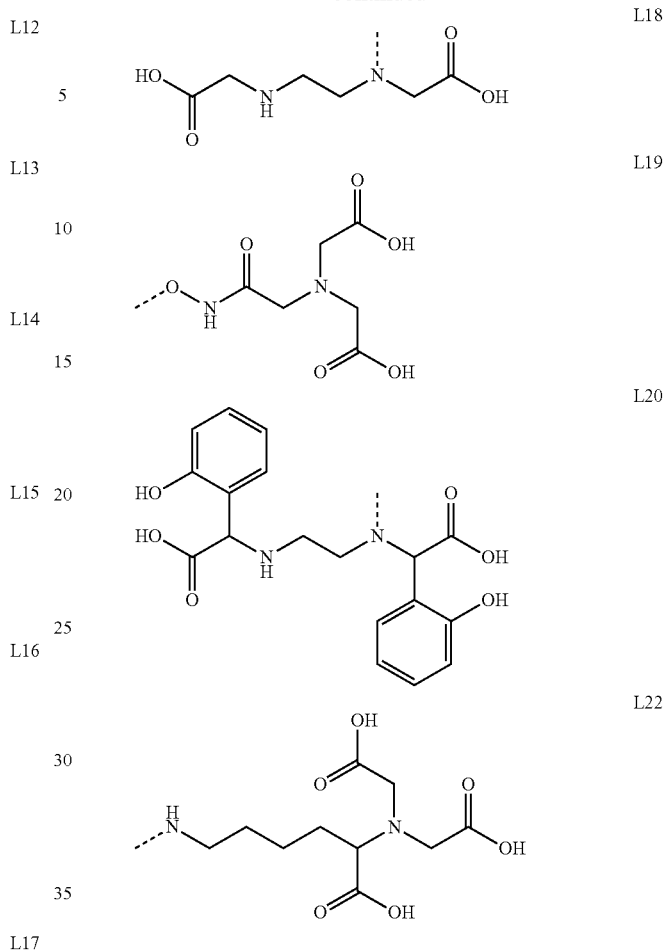

The R and R' groups in the general formula can contain at least one polymerizable moiety, for example a C=C double bond, an epoxy group, an ethyleneimine group, isocyanides, or thiol. R groups can include esters of acrylic or methacrylic acid, for example, methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate, hydroxypropyl acrylate, hydroxypropyl methacrylate, tetrahydrofurfuryl acrylate, tetrahydrofurfuryl methacrylate, glycidyl acrylate, glycidyl methacrylate, glycerol mono- and di-acrylate, glycerol mono- and di-methacrylate, ethyleneglycol diacrylate, ethyleneglycol dimethacrylate, neopentyl glycol diacrylate, neopentylglycol dimethacrylate, and trimethylolpropane triacrylate.

Other examples of R or R' can include vinyl azalactone, vinyl pyrrolidone, styrene, divinylbenzene, urethane acrylates or methacrylates, epoxy acrylates or methacrylates and polyol acrylates or methacrylates, substituted acryl amides and methacrylamides.

Examples of the R and R' group can include one or more of the following structures R1-R6:

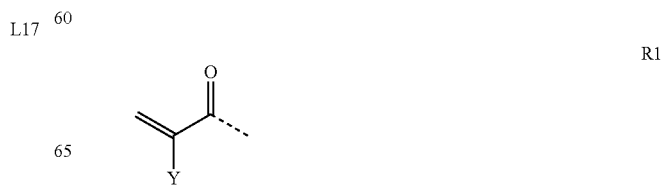

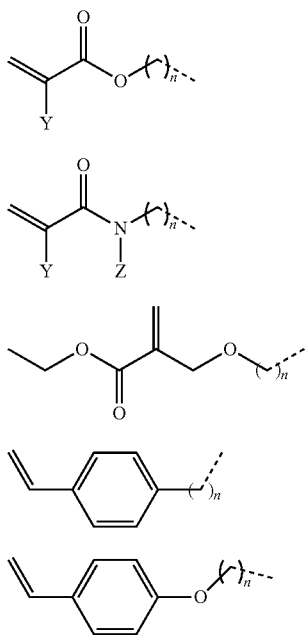

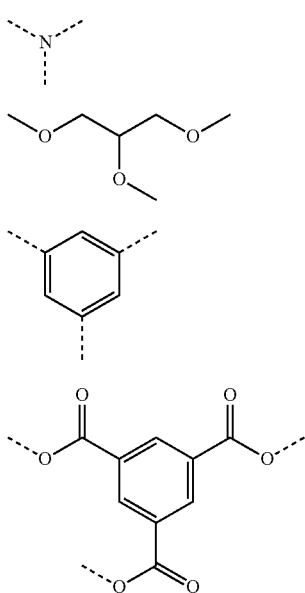

wherein a dotted line represents a bond between R (or R') and L groups (or the aliphatic chain); Y may be hydrogen or an unsubstituted aliphatic group containing 1 to 6 carbons; Y may be a methyl group; Z may be hydrogen or an unsubstituted aliphatic group containing 1 to 6 carbons; Z may be methyl or ethyl group; n may be an integer from 0 to 20.

In the general formulas (2) described herein, A can be a substituted or unsubstituted aliphatic or aromatic linkage group, such as one having 1 to 100 carbon atoms and at least three bonding sites. Non-limiting examples of the A group can include one or more of (but not limited to) the following structures A1-A11 (a dotted line represents a bond between R and L group):

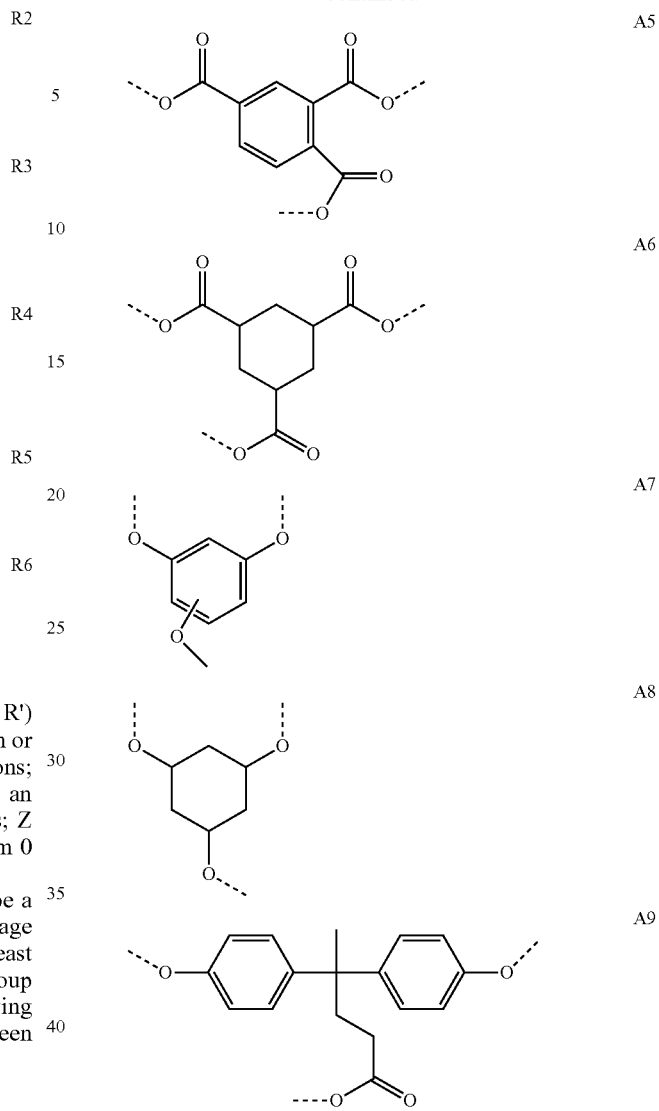

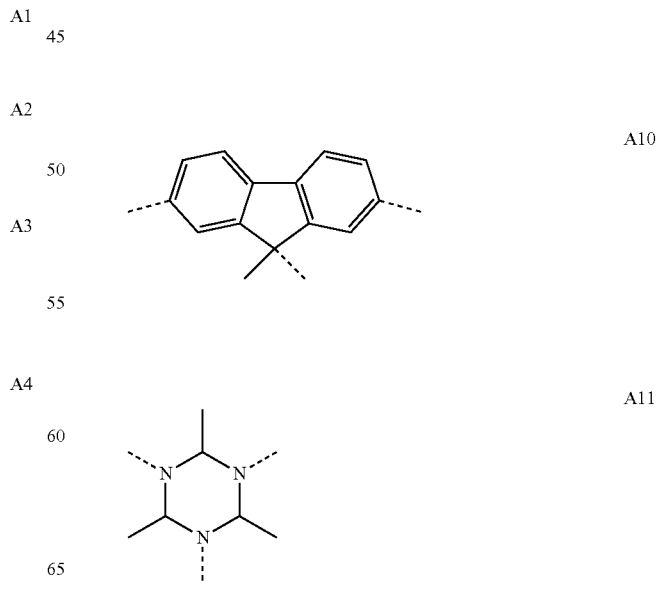

Embodiments in formulas (2) can be copolymerized with other monomers commonly used in dental materials or medical devices and/or initiators, by either heat cure, irradiation of UV or visible light (light cure), or chemical initiating agents (chemical cure or self-cure). These polymer containing gallium complexes can act as an ion exchange membrane to promote the release of gallium ion from the filler or the recharge of gallium ions from oral health care products containing gallium compounds. Curing, for example, can refer to the hardening of a polymer material as described herein by cross-linking polymer chains, that can initiated by electron beams, heat, or chemical additives.

Embodiments in formulas (2) can be copolymerized with other antimicrobial monomers or fluoride-releasing dental monomers to provide a synergistic antimicrobial and caries prevention effects. In this combination, the antimicrobial monomers and polymers can provide contact-kill of the microbes while the gallium compounds released from the material can kill or inhibit the microbes in the adjacent but not in contact with the material.

Embodiments of the present invention can include cross-linking monomers that can form 3-dimensional cross-linked polymer network with high mechanical properties and chemical stability. This characteristic is an improvement over existing antimicrobial monomers, which contain only one polymerizable group, minimizing chances of leaching out of the biomaterial.

Embodiments of the present invention can also have higher hydrolytic stability (i.e., better resistance to hydrolytic and enzymatic degradation) than current methacrylate-based antimicrobial monomers.

Embodiments of the present invention can be used in dental materials, non-limiting examples of which comprise composites, bonding agents, sealants, resin cements, liners, endodontic materials, and infiltration resins, and dental devices.

Embodiments further provide a method of application of present invention in dental materials. For example, embodiments comprise loading the gallium compounds in formulas (1) onto mesoporous silica nanoparticles (MSN), for example SBA-15 or KIT-6, or clay nanotubes, for example halloysite nanotubes, before mixing or blending with dental monomers. These gallium-loaded MSN or clay nanotubes can help disperse the gallium compounds more uniformly in the resin matrix and maintain the structure integrity and mechanical properties of the material. In an embodiment, the symbol "@" can refer to "loading on". For example, @MSN can refer to loading onto mesoporous silica nanoparticles.

Examples are given below of synthesis and characterization of several embodiments of antimicrobial gallium compounds and monomers in accordance with this invention. Examples are also given below for the fabrication and characterization of gallium-releasing experimental dental composites. All solvents were HPLC grade and were dried over 3 Å molecular sieves and reactions were run under $N_2$ atmosphere when necessary. Exact masses (electrospray ionization) were obtained with a Bruker Esquire 3000 mass spectrometer.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1—Synthesis of Water-Soluble Gallium Complexes According to Formula (1)

The water-soluble gallium complexes with fluoride, iminodiacetic acid (IDA), 2,N-(2-hydroxyethyl)iminodiacetic acid(HIDA), citric acid (CA), and ethylenediaminetetraacetic acid (EDTA) were synthesized in aqueous solutions. $Na_2GaF_6$ was synthesized using gallium (III) nitrate (0.01M, 2 mL) added drop-wise to sodium fluoride (0.05 M, 2 mL) under strong stirring. Other gallium complexes (chelates) were synthesized using the ligand (0.01M, 2 mL) reacted with gallium (III) nitrate (0.01M, 1 mL) and sodium fluoride (0.01M, 2 mL). The complexes were analyzed using ESI-MS in negative mode. The results are shown in Table 1. The $Na_2GaF_5$ solution of $2\times10^{-3}$ M is stable up to pH 5.9. All other Ga chelates of $10^{-2}$M concentration are stable at pH 6.5.

TABLE 1

List of ligands and the structures of their gallium (fluoride) complexes

| Ligand name | Iminodiacetic acid (IDA) | 2,N-(2-hydroxyethyl) iminodiacetic acid (HIDA) | Citric acid (CA) | Ethylenediamine-tetraacetic Acid (EDTA) |
|---|---|---|---|---|
| Structure | Exact Mass: 330.97 | Exact Mass: 419.02 | Exact Mass: 296.93 | Exact Mass: 356.99 |
| Measured m/z | 329.4 | 417.0 | 295.8 | 357.3 |

Example 2—Antibacterial Activities of Gallium Compounds Against Selected Bacteria The antibacterial activities of three complexes against six oral bacteria at pH 5.9 were tested by measuring the optical density (OD, at 600 nm) of the cultures in 98 cell plates of different bacteria with the presence of serial dilution of the compounds ($10^{-2}$M-$7.81 \times 10^{-5}$M) after culture at 5% $CO_2$ under 37° C. for 18 hours. The midpoint concentration (IC 50) was determined at the concentration that corresponds to 50% of maximum OD. The minimum inhibition concentration (MIC) was determined at the concentration that corresponds to 10% or less of OD of the control (without any gallium compound). The results are shown in Table 2 and Table 3. This result indicates that the mixed (ternary) gallium complexes with chelating ligands (IDA and CA) and fluoride are more effective (lower IC50 and MIC) than gallium fluoride complex ($Na_2GaF_5$). It is noted that these gallium complexes (chelates) are highly effective against *Pseudomonas aeruginosa* (very low IC50 and MIC).

or halloysite clay nanotube (HN, Advanced Materials) or KIT-6 (ACS Materials), stirring for 10 min and degassing under reduced pressure (20 mmHg) for 10 min, and repeating the stirring-degassing process five times; filtrating or centrifuging the suspension and drying the particles at 80° C. and under vacuum overnight. $Ga(OH)_3$ was loaded onto the nanoparticles by immersion of the nanoparticles in gallium nitrate ethanol solution, filtration, and sintering at 300° C. $GaF_3$ was synthesized by mixing aqueous solutions of gallium nitrate and sodium fluoride (molar ratio 1:3) and the precipitate was filtered and dried under vacuum.

b) The control composite was formulated with 30 wt % monomer mixture (BisGMA/EBPDMA/HDDMA=4:4:2, Esstech, and 1% photoinitiators) and 70 wt % silanized F-releasing glass filler (Caulk/Dentsply). The experimental composites were formulated by replacing part of the filler with different gallium-compound-loaded-nanoparticles or $GaF_3$: 5.0%, and 10%. Bar specimens (25×2×2 mm, n=12) were prepared, light cured, and placed in de-ionized water at 37° C. for 24 h. Flexural strength and flexural modulus were tested on Instron 5566 testing machine.

TABLE 2

Midpoint concentration (IC50) of three gallium compounds against six bacteria.

| | *Actinomyces naeslundii* | *Lactobacillus casei* | *Pseudomonas aeroginosa* | *Streptococcus mutans* | *Streptococcus pneuomoniae* | *Streptococcus sobrinus* |
|---|---|---|---|---|---|---|
| GaIDAF | $9.375 \times 10^{-4}$M | $>2.50 \times 10^{-3}$M | $<7.810 \times 10^{-5}$M | $6.25 \times 10^{-4}$M | $1.875 \times 10^{-3}$M | $1.25 \times 10^{-3}$M |
| GaCAF | $9.375 \times 10^{-4}$M | $>2.50 \times 10^{-3}$M | $<7.810 \times 10^{-5}$M | $6.25 \times 10^{-4}$M | $1.875 \times 10^{-3}$M | $1.25 \times 10^{-3}$M |
| $Na_2GaF_5$ | $1.875 \times 10^{-3}$M | $>5.00 \times 10^{-3}$M | $>1.875 \times 10^{-3}$M | $1.25 \times 10^{-3}$M | $1.875 \times 10^{-3}$M | $1.25 \times 10^{-3}$M |

TABLE 3

Minimum Inhibition Concentration (MIC) of three gallium compounds against six bacteria.

| | *Actinomyces naeslundii* | *Lactobacillus casei* | *Pseudomonas aeroginosa* | *Streptococcus mutans* | *Streptococcus pneuomoniae* | *Streptococcus sobrinus* |
|---|---|---|---|---|---|---|
| GaIDAF | $1.25 \times 10^{-3}$M | $>10^{-2}$M | $<7.81 \times 10^{-5}$M | $1.25 \times 10^{-3}$M | $5 \times 10^{-3}$M | $5 \times 10^{-3}$M |
| GaCAF | $1.25 \times 10^{-3}$M | $>10^{-2}$M | $<7.81 \times 10^{-5}$M | $1.25 \times 10^{-3}$M | $5 \times 10^{-3}$M | $5 \times 10^{-3}$M |
| $Na_2GaF_5$ | $2.5 \times 10^{-3}$M | $>10^{-2}$M | $5 \times 10^{-5}$M | $2.5 \times 10^{-3}$M | $5 \times 10^{-3}$M | $5 \times 10^{-3}$M |

Example 3—Formulation and Characterization of Antibacterial pH-Responsive Gallium-Releasing Dental Composites The pH-responsive gallium-releasing antibacterial experimental dental composites were prepared and characterized for their mechanical properties, gallium release, and biofilm-inhibition effect against *S. mutans* in the following procedure:

a) Preparation of nanoparticles containing the gallium compounds: Dissolving the gallium fluoride complex $Na_2GaF_5$ ($GaF_n$ for short) and gallium fluoride citrate chelate (GaCAF) in methanol saturation concentration; adding 20% w/v mesoporous silica nanoparticles (MSN, ACS Materials)

c) Gallium release in deionized water (pH7.0) and acetate buffer (pH5.5) were analyzed by spectrophotometric method.

d) Disc samples (10 mm diameter, 1.5 mm thick, n=4 for each test) were prepared. Biofilm-inhibitory effect of the composites against *S. mutans* was tested by culturing the discs in *S. mutans*-inoculated BHI medium (pH6.2), drop-plating of serial dilutions ($10^{-2}$-$10^{-5}$) of the biofilm suspensions on agar plates, and recording the colony forming units (CFU).

e) The data were analyzed using ANOVA and Tukey's HSD test ($\alpha=0.05$). The results are shown in Table 4.

TABLE 4

Mechanical properties, Ga release and CFU of S. mutans of experimental composites

| Materials | Flexural Strength MPa* | Flexural Modulus MPa* | S. mutans CFU | Cumulative gallium release in 14 days pH = 5.5 | pH = 7.0 |
|---|---|---|---|---|---|
| Control | 108.20 ± 10.66$^a$ | 6625 ± 807$^C$ | (1.96 ± 0.80) × 10$^{5*}$ | — | — |
| 5% GaF$_3$ | 86.46 ± 12.95$^b$ | 9810 ± 668$^A$ | — | — | — |
| 5.0% Ga(OH)$_3$@HN | 93.58 ± 6.58a,b | 8870 ± 773$^B$ | — | — | — |
| 5.0% GaF$_n$@HN | 101.00 ± 10.38$^a$ | 9423 ± 472$^A$ | (1.17 ± 0.17) × 10$^4$ | 57.54 ± 6.50$^b$ | 27.61 ± 1.57$^e$ |
| 10% GaF$_n$@HN | 90.51 ± 8.64$^{a,b}$ | 9479 ± 721$^A$ | (1.81 ± 0.56) × 10$^3$ | 72.91 ± 4.23$^a$ | 55.72 ± 1.96$^b$ |
| 5% GaF$_n$@MSN | 103.26 ± 8.90$^a$ | 9501 ± 643$^A$ | (4.72 ± 5.27) × 10$^3$ | 51.55 ± 2.47$^c$ | 17.26 ± 0.83$^f$ |
| 10% GaF$_n$@MSN | 93.33 ± 8.59$^{a,b}$ | 8470 ± 282$^B$ | (1.22 ± 0.38) × 10$^3$ | 61.35 ± 5.26$^b$ | 30.16 ± 1.3$^e$ |
| 5% GaCAF@MSN | — | — | (2.13 ± 0.68) × 10$^3$ | — | — |
| 10% GaCAF@MSN | — | — | (7.56 ± 1.68) × 10$^2$ | — | — |
| 15% Ga(OH)$_3$ @KIT-6 | 101.94 ± 17.79$^a$ | 7299 ± 815$^{B,C}$ | (8.50 ± 3.61) × 10$^3$ | 39.07 ± 2.23$^d$ | 15.79 ± 1.75$^f$ |

*The groups have the same superscript letter have no significant difference (p > 0.05).

Conclusion: Gallium release increases with increase of the amount of gallium complexes and decrease of pH values. Directly mixing 5% GaF$_3$ as the filler in the dental composite will reduce the mechanical properties of material. However, gallium-releasing antibacterial dental composites prepared with gallium-compound-loaded mesoporous silica nanoparticles or clay nanotube will have similar mechanical properties to the control. These gallium-releasing dental composites can inhibit the growth of S. mutans biofilm whose CFU decrease with increase of gallium content in the materials. The composites with gallium fluoride complexes or gallium fluoride citrate chelate have higher gallium release and better biofilm-inhibition effect than that with gallium hydroxide.

Example 4—Synthesis of Monomethacrylate Chelating Monomers

The monomethacrylate monomers containing various chelating group (L2, L4, L7, and L8) can be synthesized by the following scheme, where OyxmaPure® is 2-cyano-2-(hydroxyamino)acetate:

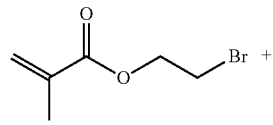

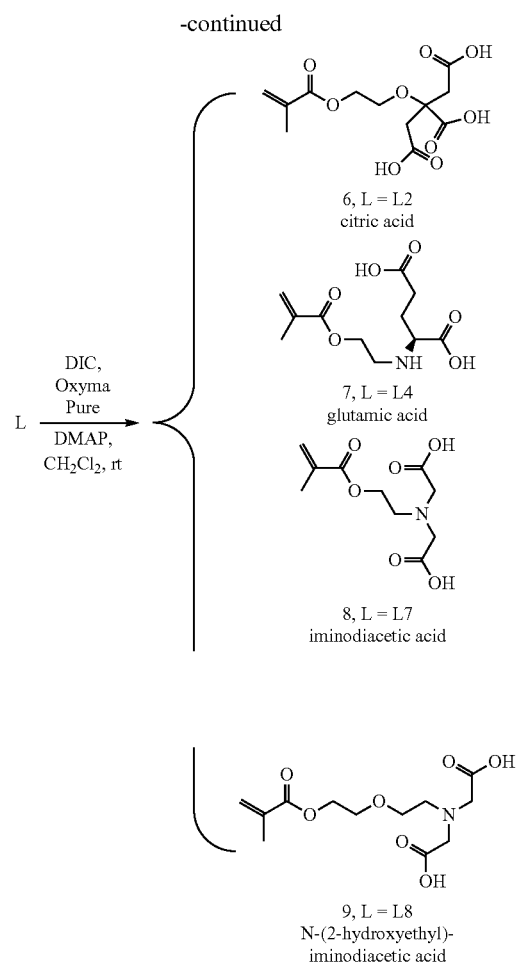

Example 5—Synthesis of Dimethacrylate Chelating Monomer with Flexible Core

The dimethacrylate monomers with flexible core containing various chelating group (L2, L7, L8, and L11) can be synthesized by the following scheme. The intermediate 12 can be first synthesized by reaction of 1,3-glycerin dimethacrylate (10) with 3-bromopropanoic acid (11) or succinic anhydride. Then reaction of various L with 12 will yield dimethacrylate chelating monomers (13-16).

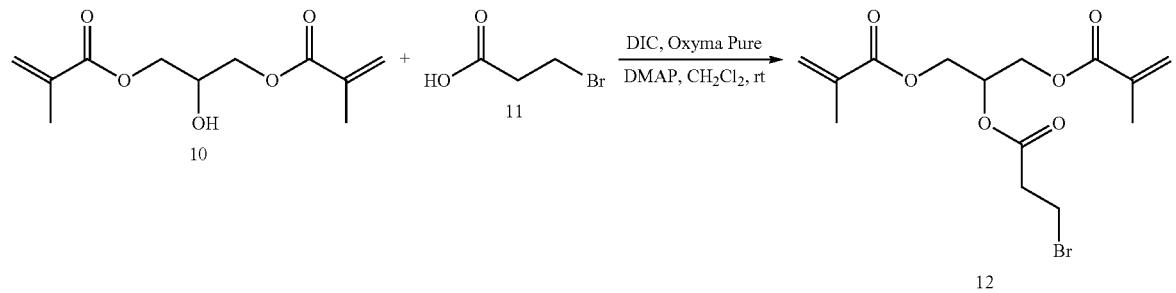

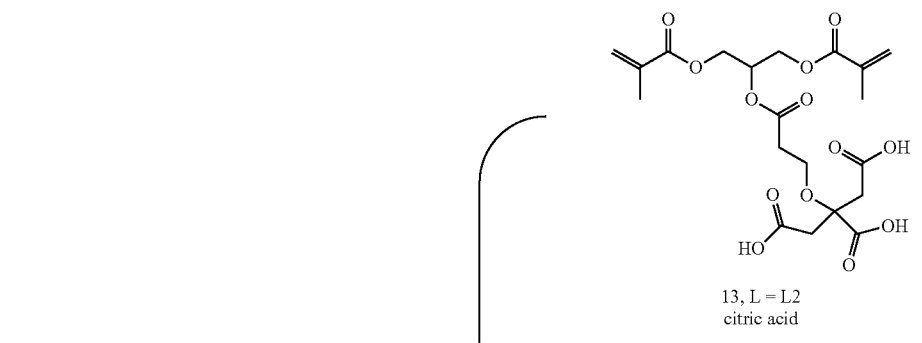

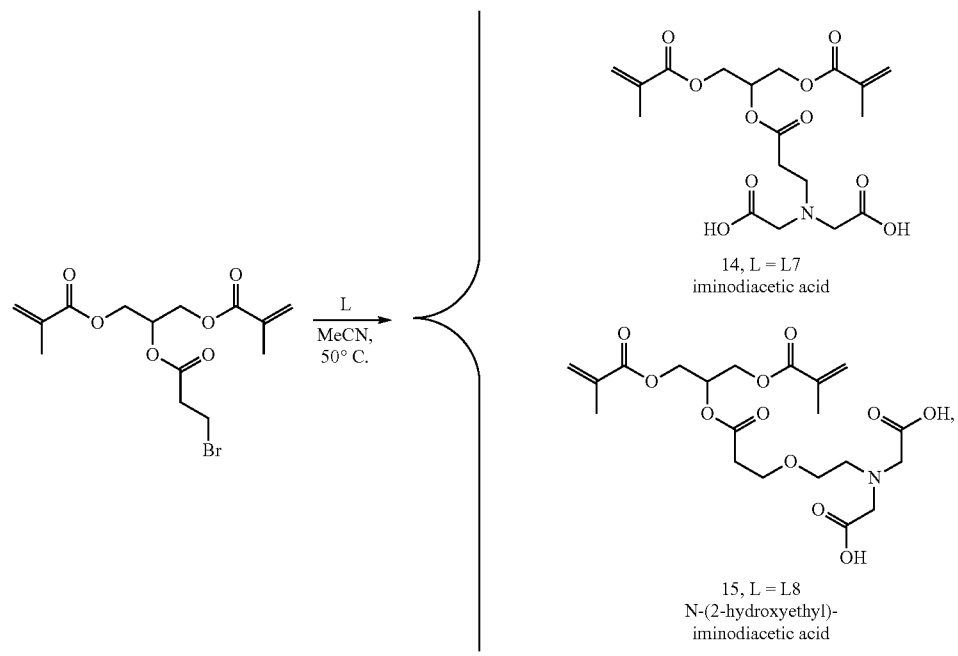

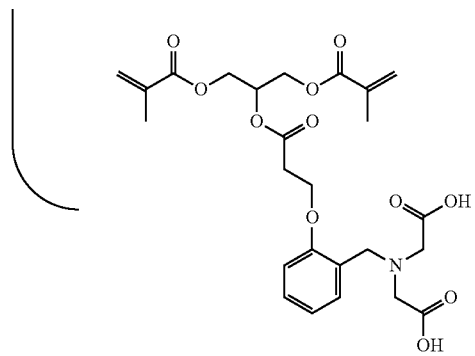

16, L = L11
N-(2-hydroxybenzyl) iminodiacetic acid

Example 6—Synthesis of Dimethacrylate Chelating Monomer Containing Rigid Core The dimethacrylate chelating monomer containing rigid (Bisphenol A) core and various chelating groups (L2, L8, and L11) can be synthesized by the following scheme. The intermediate (19) can be first synthesized by reaction of bisphonal A veneric acid (17) with bromoethylmethacrylate (18). Then the reaction of 19 with various L will generate dimethacrylate chelating monomers (20-22).

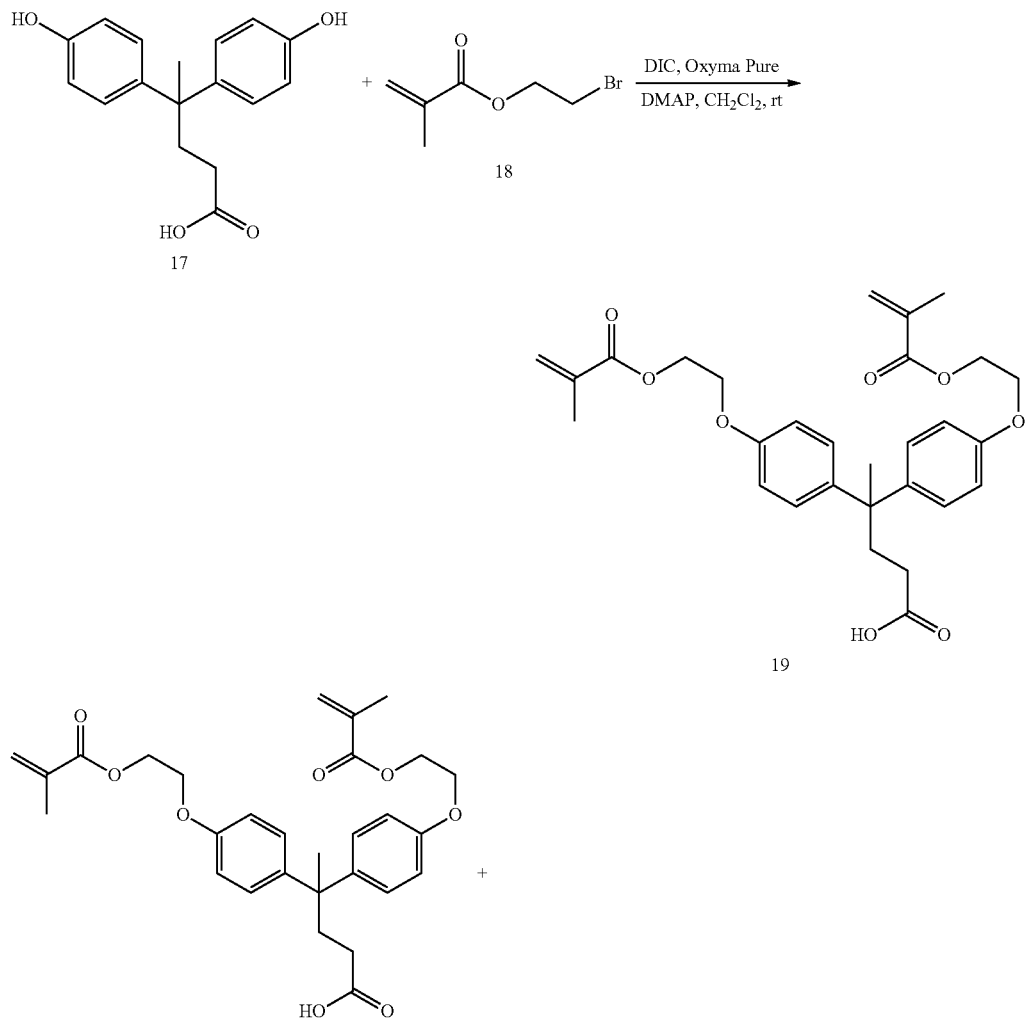

-continued
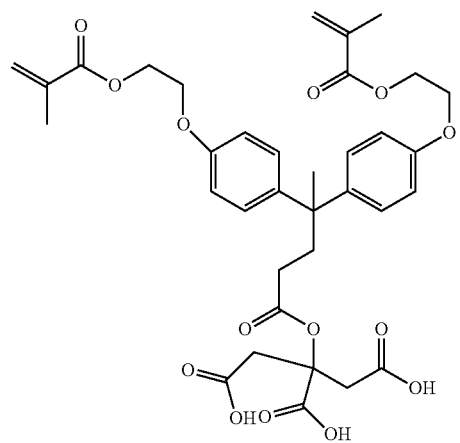
20, L = L2
citric acid
L $\xrightarrow{\text{1-methyl-2-chloro-pyridiniumiodide}}_{\text{Et}_3\text{N/DMF/100° C.}}$
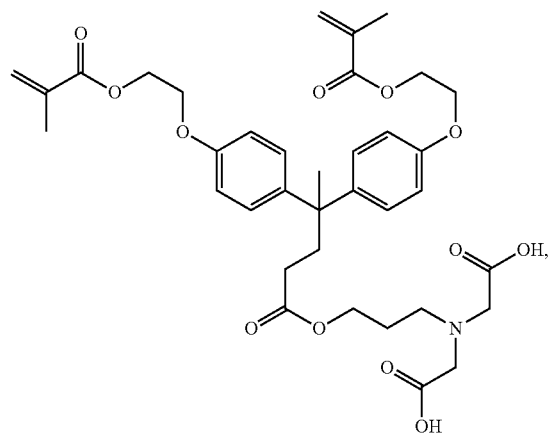
21, L = L8
N-(2-hydroxyethyl)-iminodiacetic acid
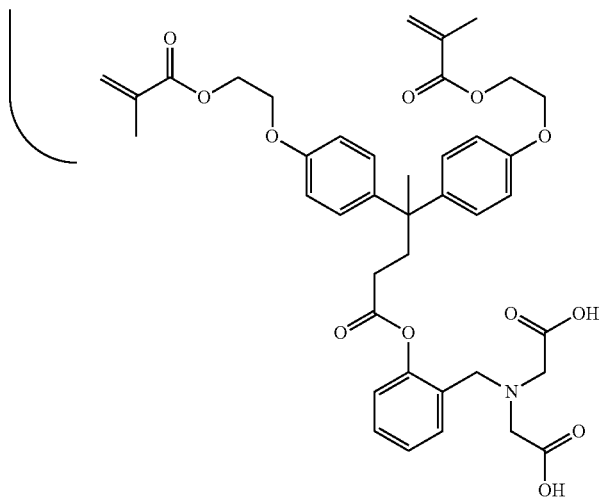
22, L = L11
N-(2-hydroxybenzyl)iminodiacetic acid

Example 7

In still other embodiments, the present invention can be used in biomedical materials and devices, such as catheter tubes, bone grafting materials, skin grafting materials, scaffolds for tissue engineering.

Other embodiments of the present invention include, but are not limited to, compounds and/or methods for: water treatment, medical and healthcare products, food applications, textile products, and/or research purposes (e.g., cell culture).

Example 8—Mechanical Properties of Antibacterial Gallium-releasing Dental Composites Described herein are methods to study the mechanical properties of antibacterial composites containing different amounts of gallium compounds.

Different nanoparticles were used as controlled-releasing and dispersing media for the gallium compounds, including mesoporous silica nanoparticles (MSN and KIT-6, ACS Materials), SBA-15 (synthesized), and halloysite nanotube (HN, Advanced Mineral). $Ga(OH)_3$ was loaded onto the nanoparticles by immersion of the nanoparticles in $Ga(NO_3)_3$-ethanol solution, filtration, and sintering at 300° C. Gallium-fluoride complex ($Na_nGaF_{3+n}$ or simply $GaF_n$) was loaded onto nanoparticles by immersion the nanoparticles in $GaF_n$-methanol solution, filtration, and drying at 80° C. under vacuum. $GaF_3$ was synthesized by mixing aqueous solutions of $Ga(NO_3)_3$ and $NaF$ (molar ratio 1:3) and the precipitate was filtered and dried under vacuum. Control composite was formulated with 30 wt % monomer mixture (BisGMA/EBPDMA/HDDMA=4:4:2, Esstech, and 1% photoinitiators) and 70 wt % F-releasing glass filler (Caulk/Dentsply). Experimental composites were formulated by replacing part of the filler with different gallium-compound-loaded-nanoparticles or $GaF_3$: 2.5%, 5.0%, and 10%. Bar specimens (25×2×2 mm, n=12) were prepared, light cured, and placed in de-ionized water at 37° C. for 24 h. Flexural strength and flexural modulus were tested on Instron 5566 testing machine. Data were analyzed using ANOVA and Tukey's HSD test ($\alpha=0.05$)

The results are shown in Table 5. Adding 5% $GaF_n$ loaded on different nanoparticles produces composites with similar flexural strength to control while adding 5% $GaF_3$ or 2.5% $Ga(OH)_3$@HN decreased the strength. All experimental groups have higher modulus than control.

Ga-releasing antibacterial dental composites can be prepared with similar mechanical properties to control.

TABLE 5

Mechanical properties of experimental composites (MPa, mean ± SD, n = 10)

| Materials | Flexural Strength* | Flexural Modulus* |
|---|---|---|
| Control | 108.20 ± 10.66$^a$ | 6625 ± 807$^C$ |
| 5% $GaF_3$ | 86.46 ± 12.95$^b$ | 9810 ± 668$^A$ |
| 2.5% $Ga(OH)_3$@HN | 83.11 ± 6.96$^b$ | 8087 ± 250$^B$ |
| 5.0% $Ga(OH)_3$@HN | 93.58 ± 6.58$^{a,b}$ | 8870 ± 773$^B$ |
| 5.0% $GaF_n$@HN | 101.00 ± 10.38$^a$ | 9423 ± 472$^A$ |
| 10% $GaF_n$@HN | 90.51 ± 8.64$^{a,b}$ | 9479 ± 721$^A$ |
| 5% $GaF_n$@MSN | 103.26 ± 8.90$^a$ | 9501 ± 643$^A$ |
| 10% $GaF_n$@MSN | 93.33 ± 8.59$^{a,b}$ | 8470 ± 282$^B$ |
| 15% $GaF_n$@KIT-6 | 101.94 ± 17.79$^a$ | 7299 ± 815$^{B,C}$ |

*The groups have the same superscript letter have no significant difference (p > 0.05)

Example 9—Mechanical Properties of Antibacterial Dental Composites Containing Gallium Compounds Dental composites have great success as an alternative restorative material to amalgam. However, they usually have a shorter service life than amalgam. Secondary caries is the leading cause for the failure of composite restorations. Therefore, the composites with antibacterial and biofilm-inhibitory effect would have longer service life. However, their mechanical properties and physical properties (for example, color and translucency) must be maintained and meet the ADA Specifications and ISO standards. Composites containing silver nanoparticles usually have strong antibacterial effects but they have a dark shade and thus are unacceptable in dental clinic. Gallium compounds have antimicrobial effects and many of them are colorless [1-3]. Gallium-releasing dental composites have not been reported.

Methods described herein examine the mechanical properties and color index of experimental antibacterial composites containing different amounts of gallium hydroxide or gallium-fluoride complexes 1. Preparation of Gallium-Releasing Nanoparticles.

Different nanoparticles were selected to be used as a controlled releasing and dispersing media for the gallium compounds. The nanoparticles included: two mesoporous silica nanoparticles (MSN, KIT-6, ACS Materials), and Halloysite Nanotube (HN) (Advanced Mineral). Gallium hydroxide was loaded onto the nanoparticle by immersion of the particles in $Ga(NO_3)_3$ ethanol solution, filtration, and sintering at 300° C. Gallium fluoride complex was loaded onto the nanoparticles by immersion in $NaGaF_4$ methanol solution, filtration, and drying at 80° C. under vacuum.

2. Preparation of Experimental Composites.

Control composite was prepared with 30 wt % monomer mixture (BisGMA/EGMA/HDDMA/UEDMA=4:3:2:1 and 1% photoinitiators) and 70 wt % F-releasing glass filler (Caulk/Dentsply). Experimental composites were formulated by replacing part of the filler with different gallium-compound-loaded-nanoparticles: 2.5%, 5.0%, and 10%. Bar specimens (25×2×2 mm, n=12) were prepared, light cured, and placed in de-ionized water at 37° C. for 24H.

3. Mechanical Testing.

Flexural strength and flexural modulus were tested using 3-point-bending device on Instron 5566 testing machine with crosshead speed of 1 mm/min.

4. Color Index measurement.

The color index (L*, a*, b*) of light cured composite discs (10 mm dia., 1 mm thick, n=5) was measured using Chroma Meter CR-400 (Konica Minolta).

Referring to FIG. 1, the data shows that the experimental gallium-releasing composites have similar color indices compared to the control.

Figure 2:
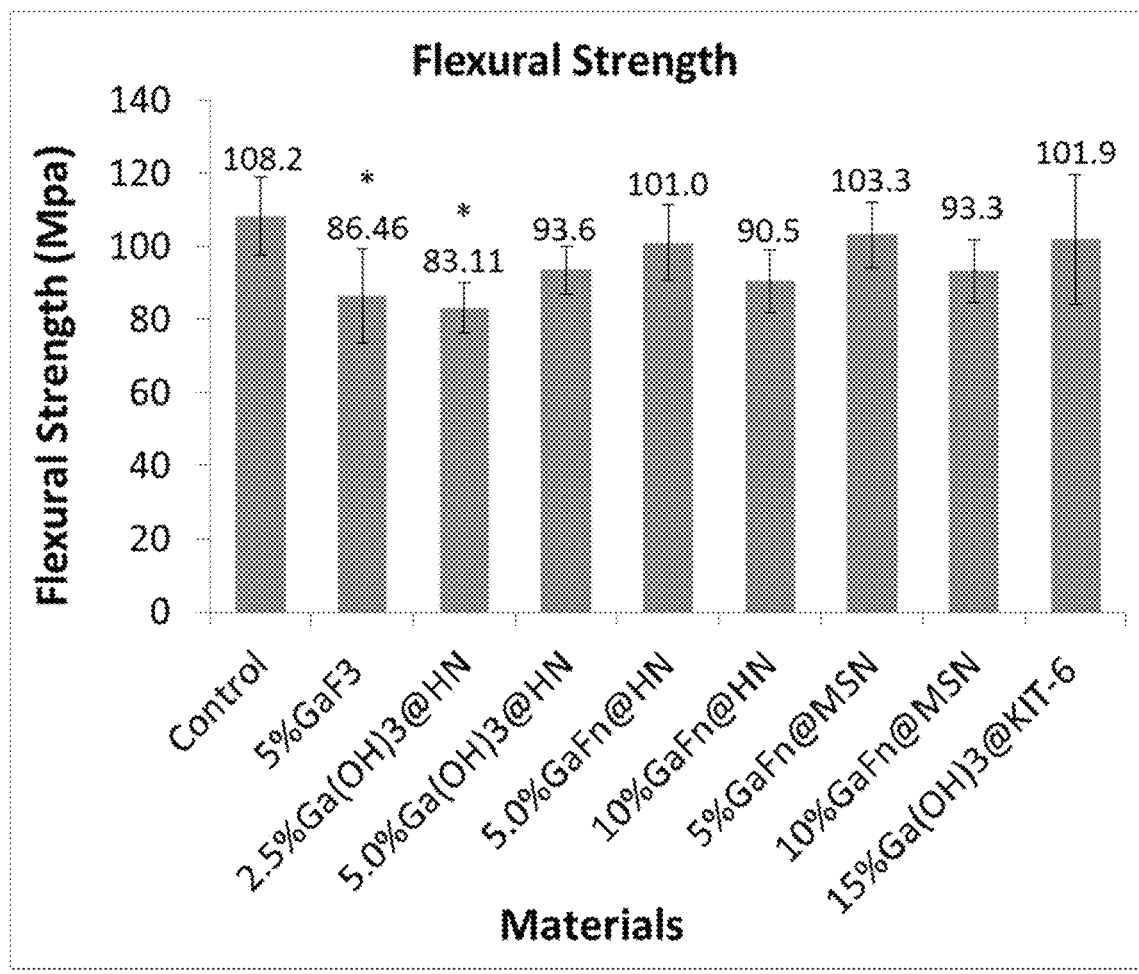
FIG. 2 shows flexural strength and flexural modulus of composites. *indicates significant difference (p<0.05). The groups with the same letter have no significant difference (p>0.05).

Referring to FIG. 2, the experimental composite have similar flexural strengths to the control (p>0.05) except for 5% $GaF_3$ and 2.5% $Ga(OH)_3$@HN, which have lower flexural strength. 5.0% $GaF_n$@HN, 5% $GaF_n$@MSN, and 15% GaFN@KIT-6 had the greatest flexural strengths of the experimental composites. The experimental composites have higher flexural modulus than the control (p<0.05).

Thus, it is possible to prepare gallium-releasing antibacterial dental composites that have similar physical and mechanical properties to the control dental composite.

REFERENCES CITED IN THIS EXAMPLE

[1] Minandri F, et al., Promises and failures of gallium as an antibacterial agent. Future Microbiology 2014, 9(3): 379-397.
[2] Valappil S P, et al., Effect of Gallium on Growth of Streptococcus mutans NCTC 10449 and Dental Tissues. Caries Res, 2014; 48:137-146.
[3] Xu X. Antimicrobial Gallium Compounds and Methods. U.S. Patent Application No. 62/635,243, Feb. 26, 2018.
[4] Wang Y., Samoei G K, Lallier T E and Xu X. Sythesis and Characterization of New Antibacterial Fluoride-releasing Monomer and Dental Composite. ACS Macro Letters 2012, 2(1):59-62.

Example 10—Formulation and Characterization of Antibacterial Gallium-Releasing Dental Composites Introduction Resin-based dental composites have been widely used in dentistry to restore carious teeth because they are tooth-colored and lack of hazardous metals. Dental composites have limited service life 9-7 years). Failed restorations accounts for 60% of dental operation. The two leading causes for the failure of dental composite restorations in clinic are secondary (recurrent) caries and bulk fracture. To reduce secondary caries, the dental composites that release anti-caries agents and have biofilm inhibitory effect are being developed.

Methods for Developing Anticariogenic Composites and Limitations

Composites that release soluble anticariogenic agents (F, Ca, P ions, CHX, for examples of anticariogenic agents and compositions see PCT/2016/194692 and U.S. Pat. No. 3,532,787)—short time, insufficient efficacy, low mechanical properties.

Antibacterial monomers and polymers containing quaternary ammonium, pyridinium, phosphonium, and sulfonium salts—have only surface antibacterial (contact-kill) effect, can be overwhelmed by bacterial biofilms or protein adsorption.

Metal (Ag, Cu, Bi, etc) compounds or nanoparticles—poor esthetics and color stability (even at very low level).

Gallium (III) Compounds as Antimicrobial Agents

Ga(III) compounds have been used as in cancer diagnosis and treatment for more than three decades.

Many life-threatening bacteria, e.g., $P.\ aeruginosa$ and $M.\ tuberculosis$, are highly susceptible to Ga(III). Oral bacteria $P.\ gingivalis$ and $S.\ mutans$ are also susceptible. (see, for example, Sahdev R, et al., J Biomater Appl 2015, 30(1) 85-92; and Valappil S P, et al., Caries Res, 2014; 48:137-146).

Gallium (III) works like a "Trojan horse" to disrupt bacterial iron (Fe(III)/Fe(II)) metabolism.

Gallium compounds have low toxicity. Ganite® is FDA approved.

Many gallium compounds are colorless-higher amount can be used in dental composites.

Challenges for Use Ga Compounds as Filler in Dental Composites

Solubility of Ga(III) compounds:
$Ga_2O_3$—insoluble
$Ga(OH)_3$—sparingly soluble, $K_{sp}=[Ga^{3+}][OH^-]^3=3.28\times10^{-36}$ $GaF_3$—sparingly soluble, 0.002 g/L, $1.58\times10^{-5}$ M
$Ga(NO_3)_3$—highly soluble Stability and bioavailability of Ga(III) in aqueous media, forming $Ga(OH)_3$ precipitate at pH>5.

Hard to disperse Ga compounds uniformly in the resin matrix-potential adverse effect on mechanical properties.

These methods will investigate the, gallium release, fluoride release, and antibacterial activity of experimental dental composites containing different gallium compounds. For example, using gallium fluoride complexes to increase solubility and stability of Ga(III) ions in aqueous solution. As another example, using mesoporous silica nanoparticle (MSN) and halloysite nanotubes (HN) as controlled releasing and dispersing media in dental composites.

Figure 3:
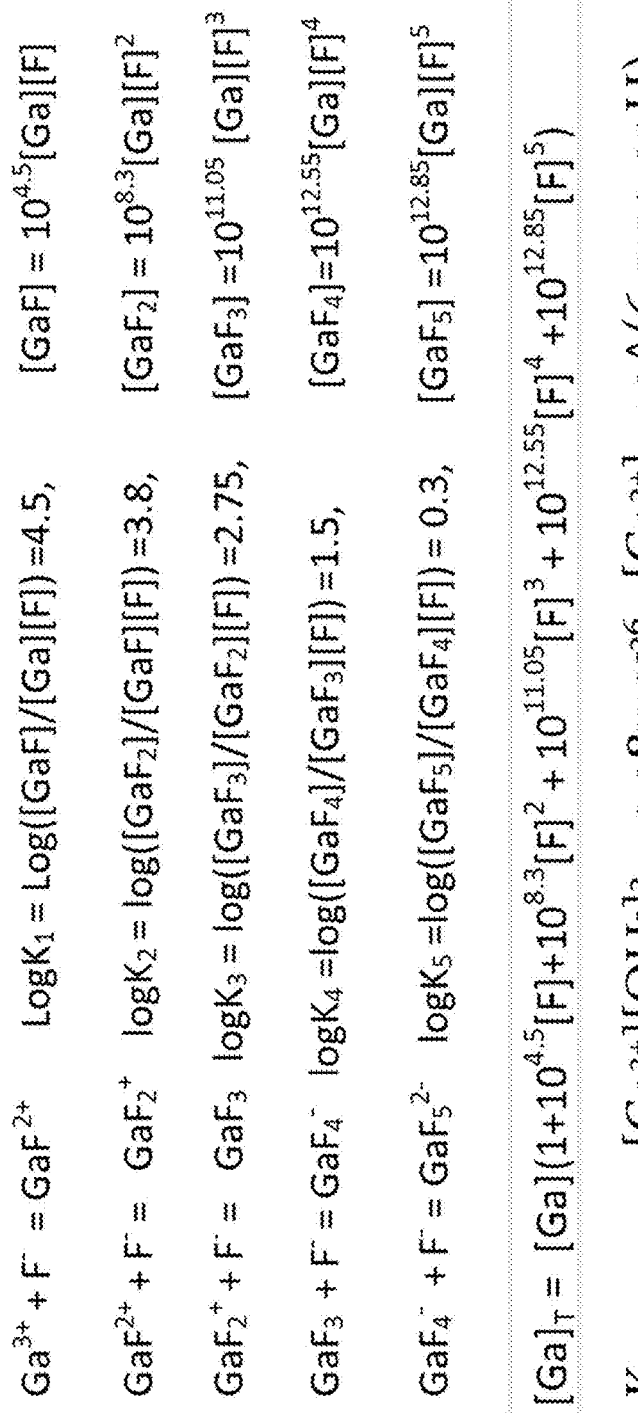
FIG. 3 shows methods of the invention.
Figure 4:
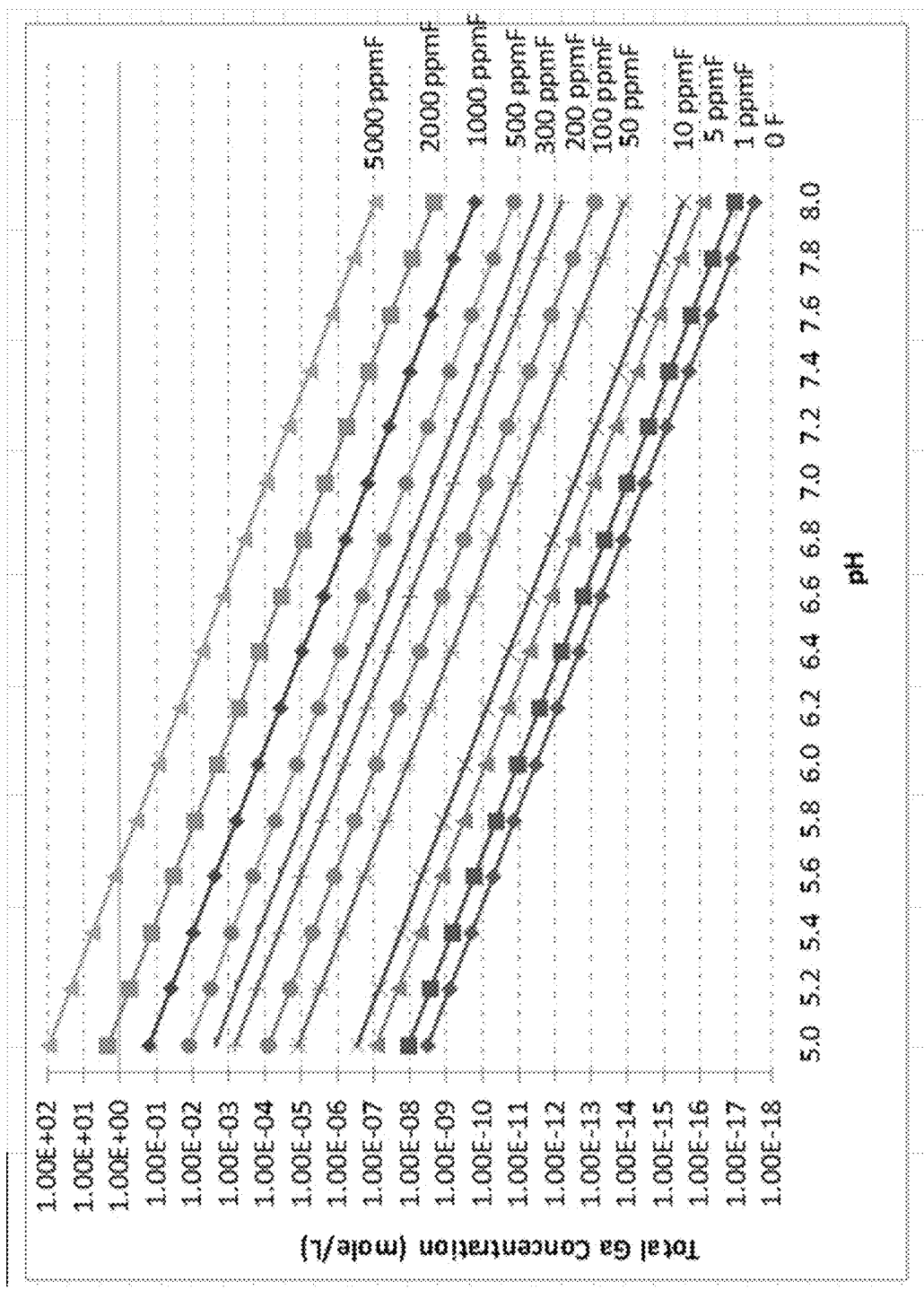
FIG. 4 shows correlation of $[Ga]_T$ with pH and $[F^-]$. $[Ga]_T = 10^{\wedge}(6.5159 - 3*pH)(1 + 10^{4.5}[F] + 10^{8.3}[F]^2 + 10^{11.05}[F]^3 + 10^{12.55}[F]^4 + 10^{12.85}[F]^5)$
Figure 5:
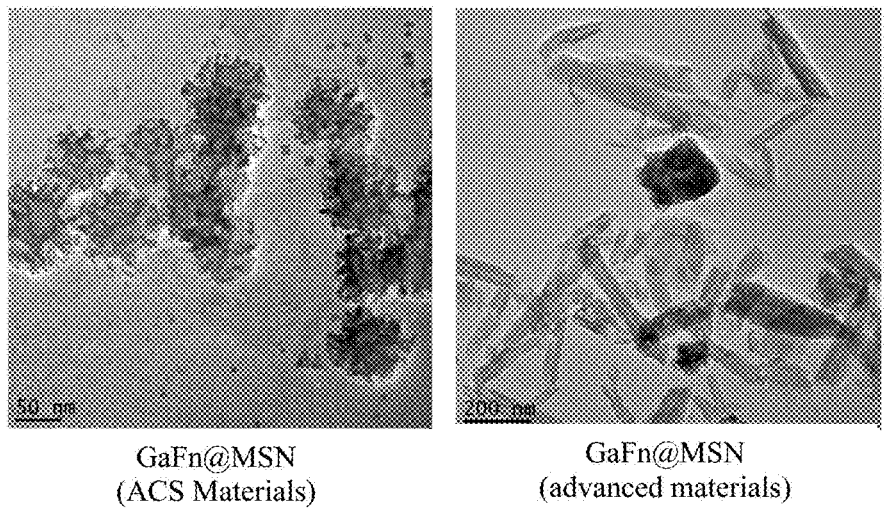
FIG. 5 shows TEM images of MSN and HN loaded with Ga—F complex.
Figure 5:
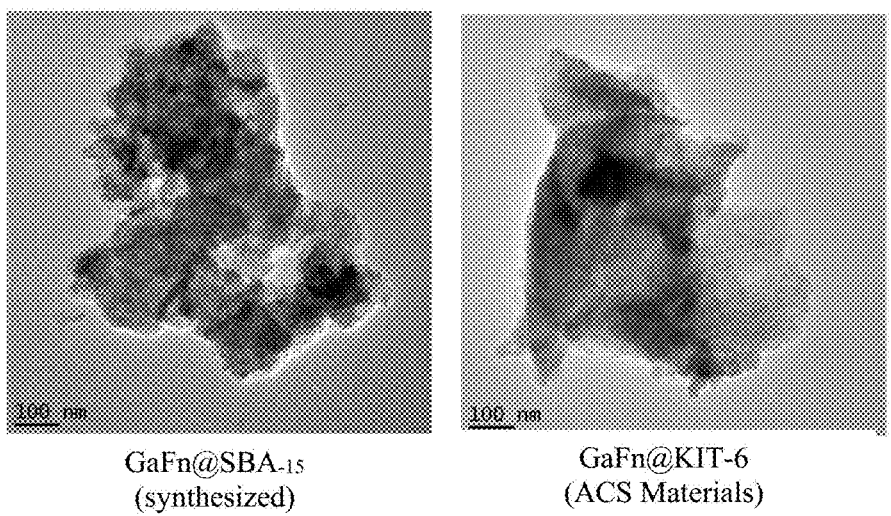
Figure 6:
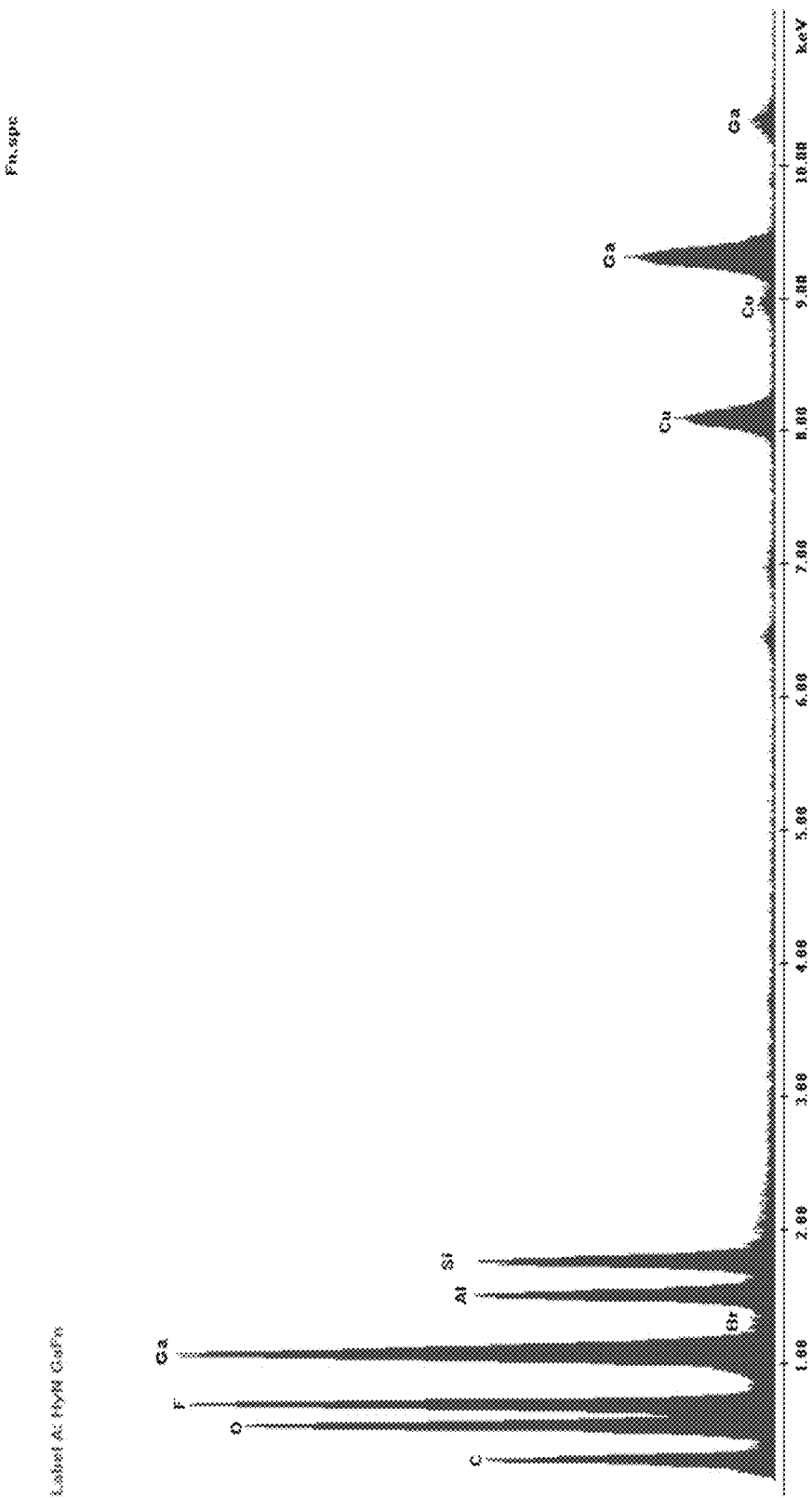
FIG. 6 shows EDS Analysis of $GaF_n$@HN.
Figure 8:
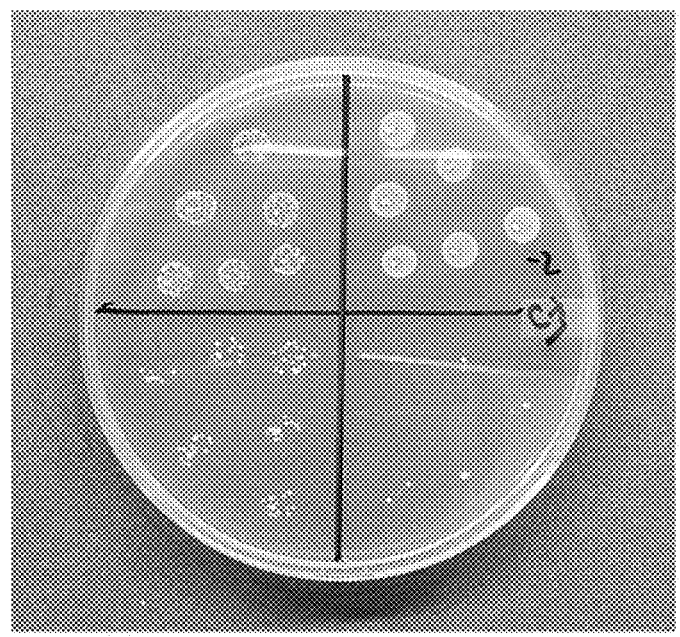
FIG. 8 shows biofilm culture.
Figure 9:
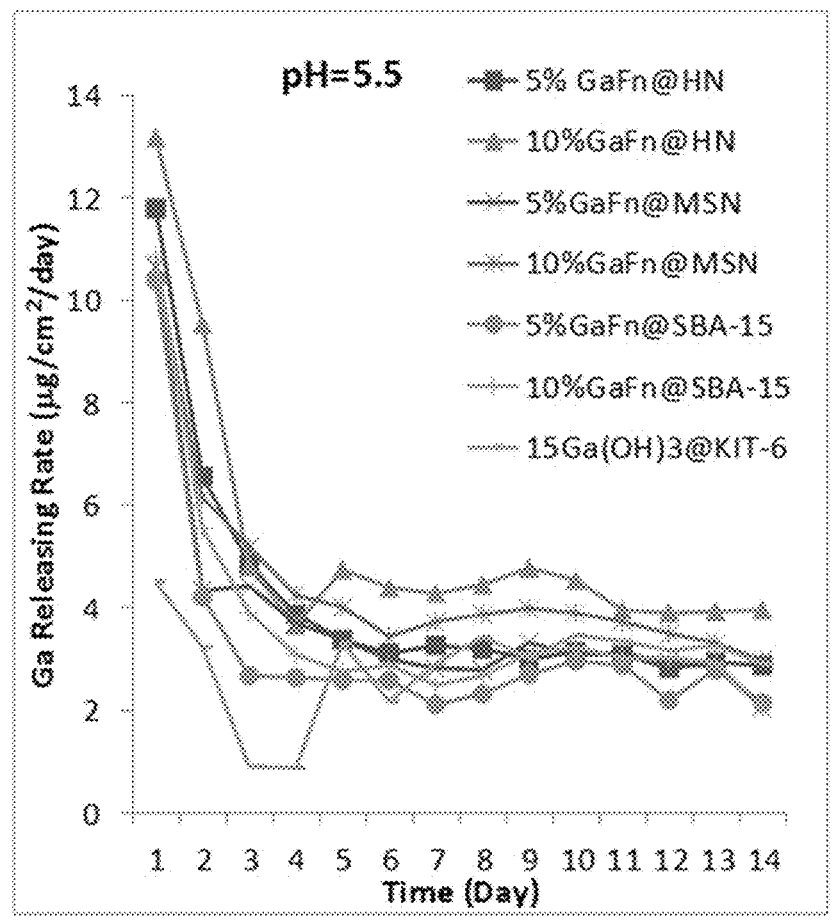
FIG. 9 shows Ga release profile.
Figure 10:
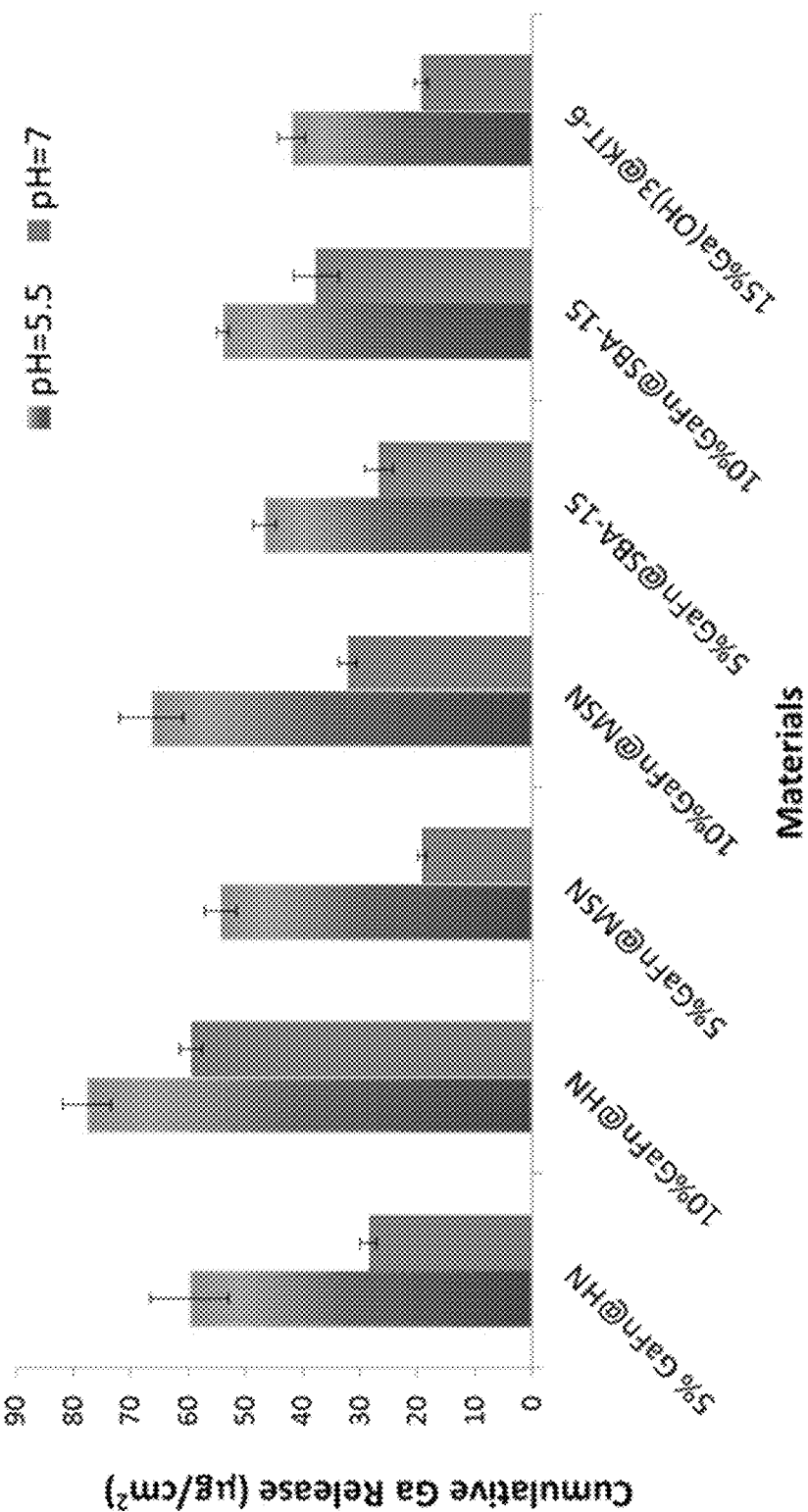
FIG. 10 shows cumulative Ga release over 35 days. The pH has great influence on gallium release (pH=5.5>pH=7). Composites with gallium fluoride complexes loaded on HN and MSN release more gallium than those with SBA-15 and Ga(OH)$_3$@KIT-6.
Figure 11:
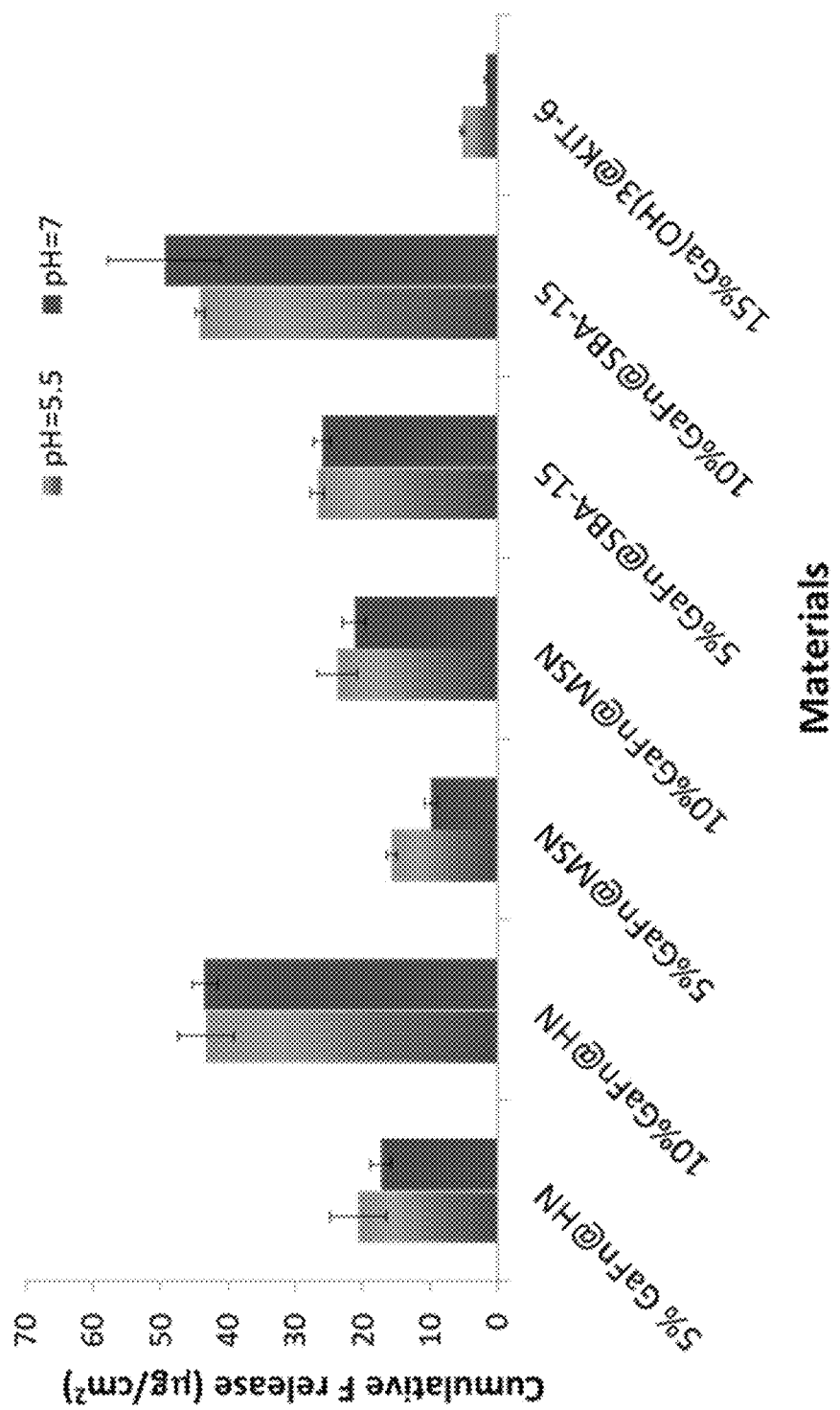
FIG. 11 shows cumulative fluoride release in 14 days. pH value does not have significant effect on fluoride release.
Figure 12:
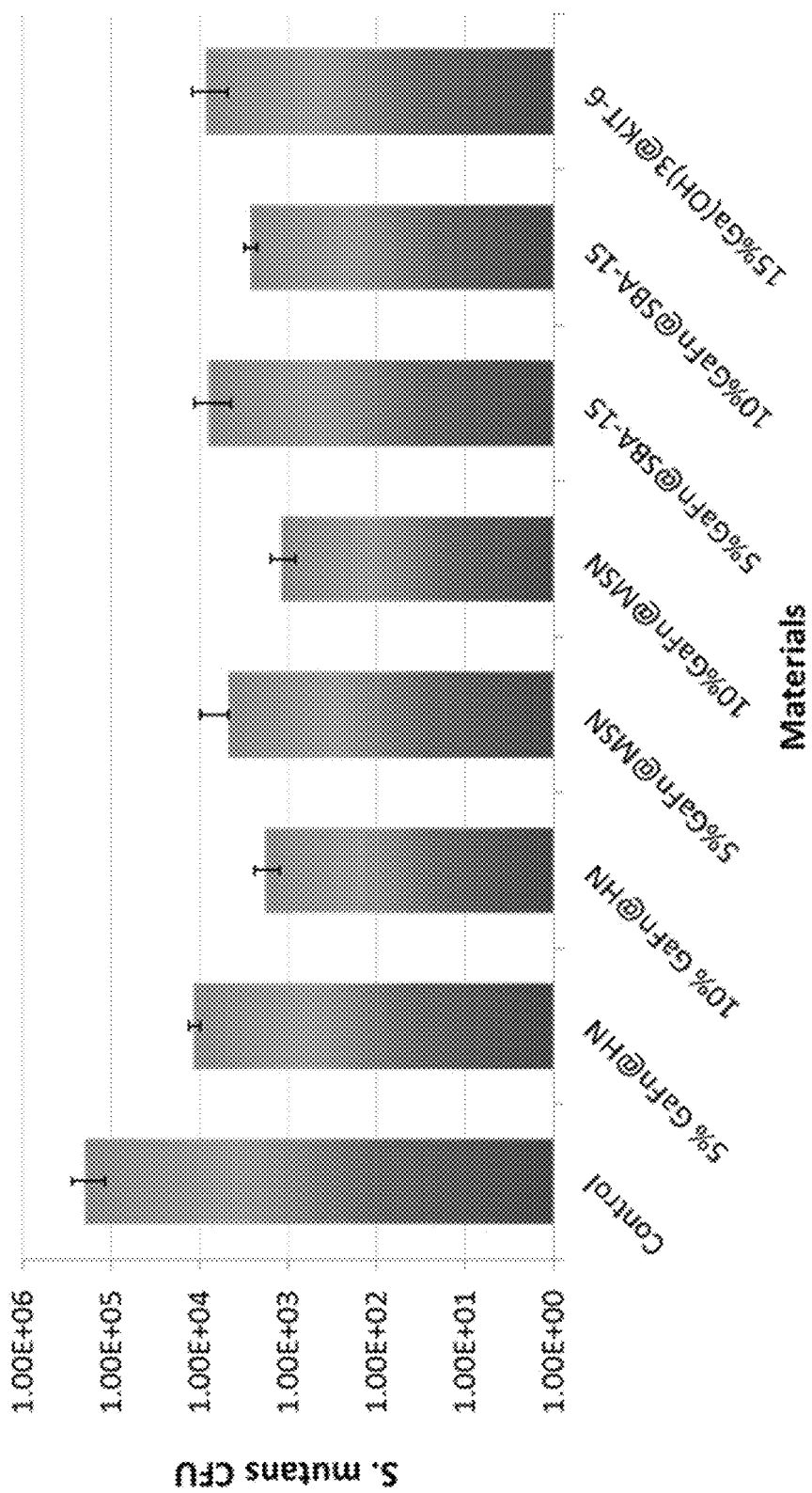
FIG. 12 shows biofilm-inhibitory effect of Ga-releasing composites. All experimental composites have significant biofilm-inhibitory effects (lower bars are better). Composites with gallium fluoride complexes loaded on HN and MSN have higher antibacterial effect than those with SBA-15 and Ga(OH)$_3$@KIT-6.

Methods see FIG. 3, for example.

Preparation of Ga-releasing nanoparticles:

Dissolve $Ga(NO_3)_3$ or $NaGaF_4$ in methanol.

Load the Ga compounds in different MSN and HN.

Dry the $NaGaF_4$-loaded nanoparticle or HN at 80° C. under vacuum.

Calcinate $Ga(NO_3)_3$-loaded nanoparticle at 300° C. in air to convert it to $Ga(OH)_3$ Ga and F Release Disc samples (10 mm diameter, 1.5 mm thick, n=4 for each test) were prepared, light cured and polished.

Gallium release in deionized water (pH7.0) and acetate buffer (pH5.5) were analyzed daily for 14 days and weekly for 4 weeks by spectrophotometric method.

Fluoride release in pH 5.4 buffer and deionized water (pH7) was analyzed using fluoride ISE.

Biofilm Culture

Biofilm-inhibitory effect of the composites against $S.\ mutans$ biofilms was tested by culturing the discs in $S.\ mutans$-inoculated BHI medium (pH6.2), drop-plating of serial dilutions ($10^{-2}$-$10^{-5}$) of the biofilm suspensions on agar plates, and recording the colony forming units (CFU) after 36 h.

The data were analyzed using ANOVA and Tukey's HSD test ($\alpha=0.05$).

Conclusions

Dental composites containing mesoporous silica or halloysite loaded with gallium compounds have pH-responsive gallium release and significant biofilm-inhibitory effects. Composites with gallium fluoride complexes have higher antibacterial effect than those $Ga(OH)_3$.

HN and MSN seem to be better controlled release media than SBA-15.

Example 11—Synthesis of a Ternary Gallium-Fluoride Chelate Using Chelating Dimethacrylate Monomer and Gallium Fluoride Complex The following examples demonstrate the synthesis of a ternary gallium-fluoride chelate using chelating dimethacrylate monomer and gallium fluoride complex and its application in dental composites to increase gallium release and biofilm inhibition effect of the material.

Synthesis of monogallium(III) mono(2,2'-((5-(4,4-bis(4-(2-(methacryloyloxy)ethoxy)phenyl)pentanamido)-1-carboxylatopentyl)azanediyl)diacetate)

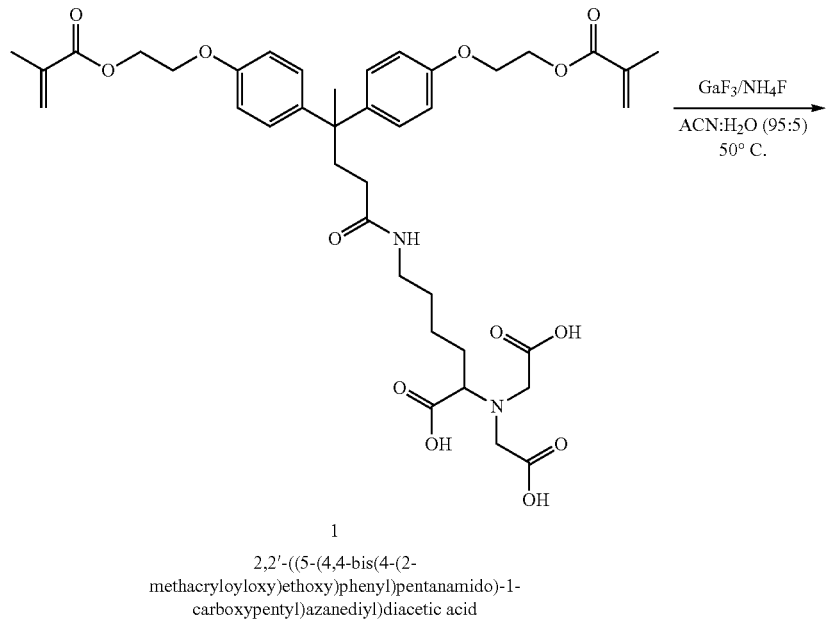

1
2,2'-((5-(4,4-bis(4-(2-methacryloyloxy)ethoxy)phenyl)pentanamido)-1-carboxypentyl)azanediyl)diacetic acid

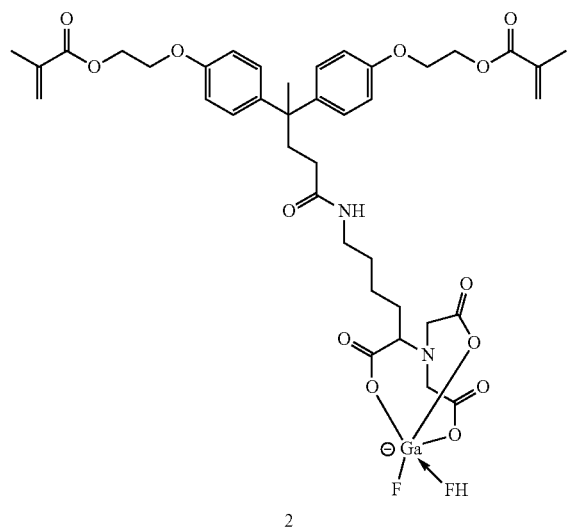

2
monogallium(III) mono(2,2'-((5-(4,4-bis(4-(2-(methacryloyloxy)ethoxy)phenyl)pentanamido)-1-carboxylatopentyl)azanediyl)diacetate) monofluoride hydrofluoride ("chelate")

monofluoride hydrofluoride (2) is shown in the scheme below. The structure of the chelate (2) has been confirmed by mass spectrometry.

Scheme: Synthesis of a Ternary Gallium-Fluoride Chelate

The chelating dimethacrylate dental monomer (1) was synthesized using the previously reported method (Wang Y, Samoei G K, Lallier T E and Xu X. Synthesis and Characterization of New Antibacterial Fluoride-releasing Monomer and Dental Composite. ACS Maco Letters 2012, 2(1):59-62). The monomer (1) was dissolved in acetonitrile-water (95:5) and gallium fluoride (1 g) prepared in the lab was added and stirred the reaction at 50 C for 48 h. The pH of the reaction mixture was maintained between 4 to 5 by adding ammonium fluoride. The organic layer was evaporated on rotary evaporator and dried under vacuum at room temperature for overnight and then at 45° C. for 2 h to yield the ternary gallium fluoride chelate (2).

In another embodiment, synthesis of gallium (III) sodium (2,2'-((5-(4,4-bis(4-(2-(methacryloyloxy)ethoxy)phenyl)

pentanamido)-1-carboxylatopentyl)azanediyl)diacetate) fluoride hydrofluoride (2) is shown in the scheme below. The structure of the chelate (2) silica nanoparticles loaded with gallium-fluoride complex (GaFn@MSN). (3) Experimental composite containing the same filler and photoinitiators as the composite (2) but its

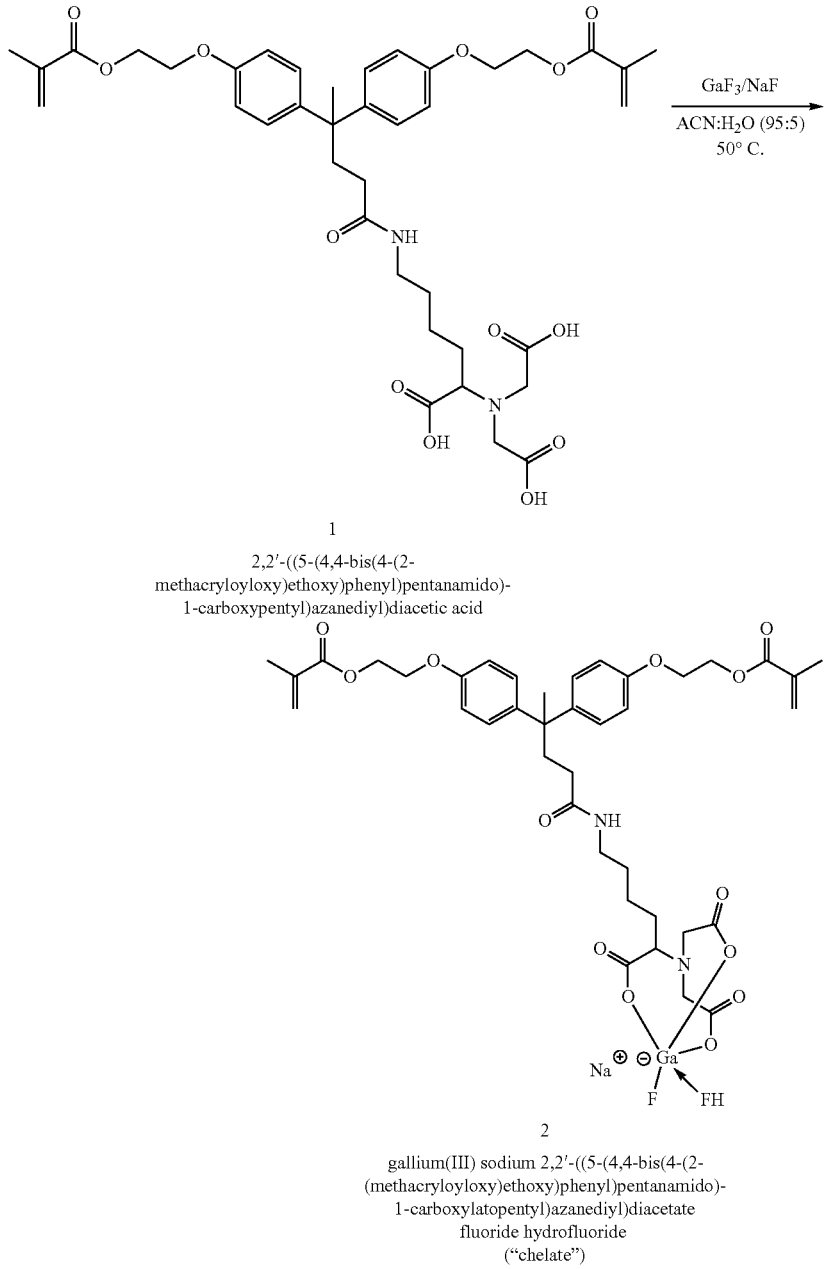

Scheme: Synthesis of a ternary gallium-fluoride chelate is based on Formulas 2, where R and R' are R2; A is A9; L is L19; M is sodium, X is fluoride. Its structure has been confirmed by mass spectrometry. This compound has not been reported in gallium releasing composition.

Three experimental dental composites were formulated: (1) Control composite containing 29 wt % mixture of dental monomers of BisGMA, EBPADMA and HDDMA (4:3:3), 70 wt % commercial fluoride-releasing filler particles and 1% photoinitiators. (2) Experimental composite containing the same monomers and photoinitiators as the control but the 10 wt % of its filler was replaced with 10% mesoporous monomers containing 15% of the ternary gallium fluoride chelate in scheme 1. The disc specimens (100 diameter, 1.5 mm thick, n=5) for analysis of gallium release and biofilm inhibition effect or bar specimens (2×2×25 mm) for flexural strength and modulus tests were prepared in separate molds and light cured for 40 s each side.

Figure 13:
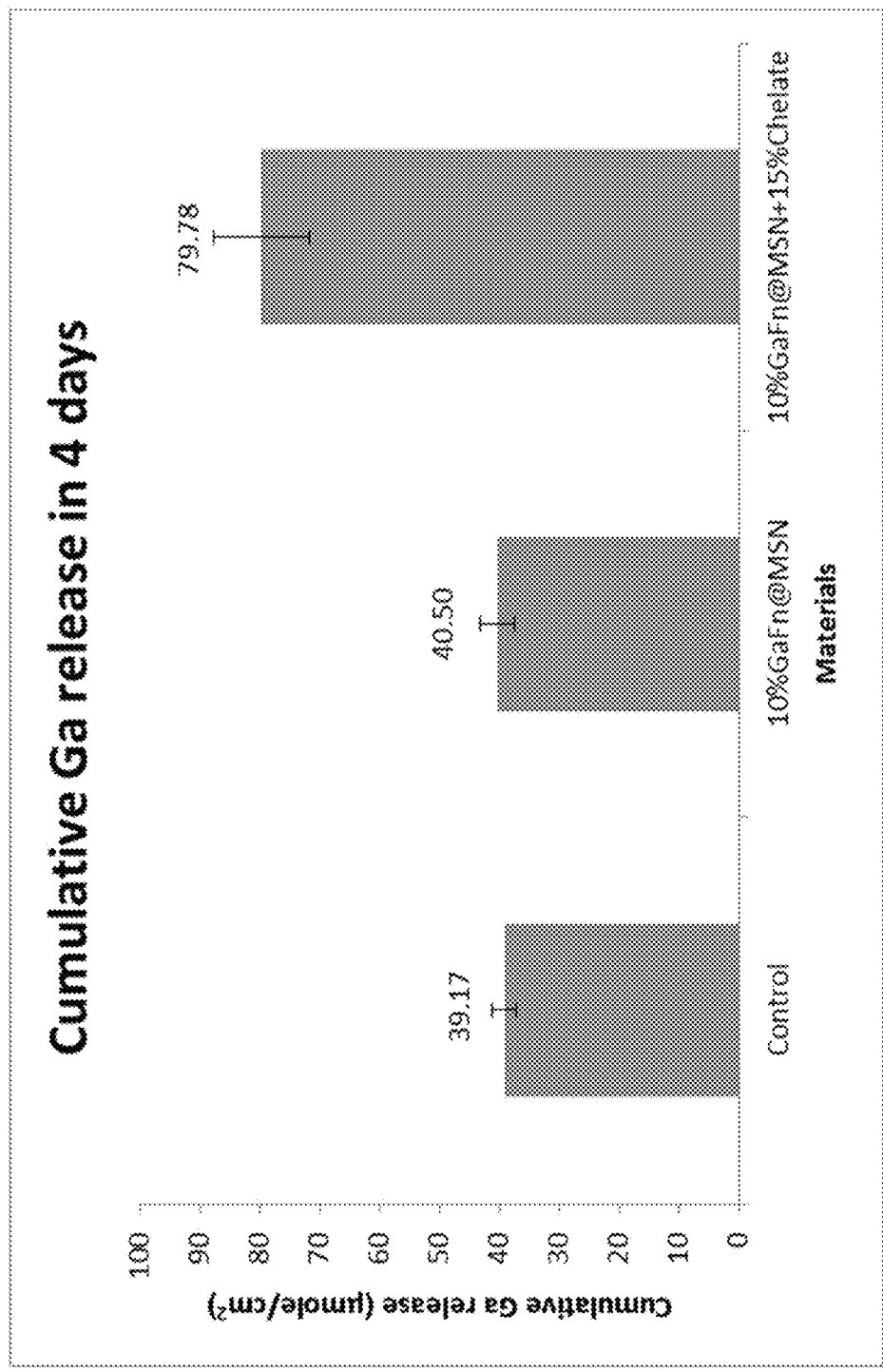
FIG. 13 shows cumulative gallium release from composite in 4 days at pH 7.0.

The gallium release from the experimental composite disc specimens (n=5) in 5 mL of deionized water (pH=7.0) was analyzed using a spectrophotometric method. The result is shown in FIG. 13. This result demonstrates that incorporation of 15% the ternary gallium fluoride chelate in the monomer could significantly increase (nearly double) the amount of gallium ion released from the material, compared with those without the chelate.

Figure 14:
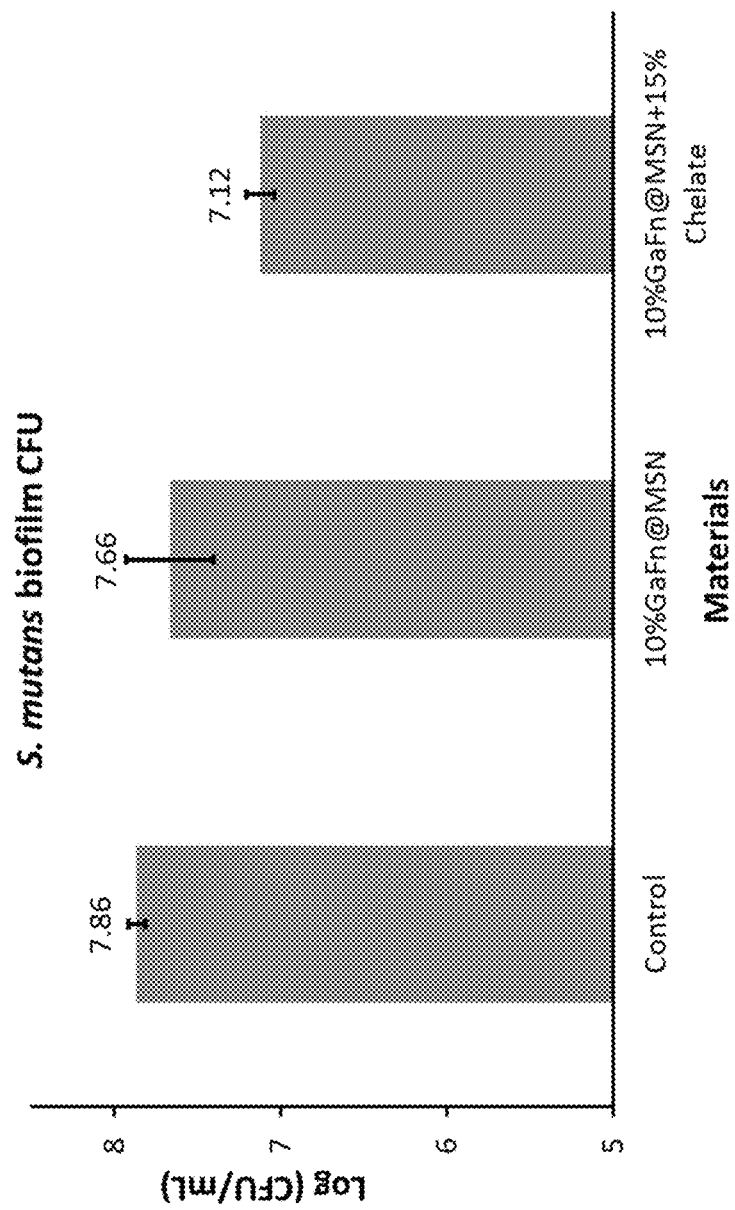
FIG. 14 shows colony formation unit (CFU) of *S. mutans* on composites.

The biofilm inhibition effect against the oral bacteria *Strep. mutans* was tested using the standard bacterial biofilm culture and drop plating method. The result is shown in FIG. 14. It shows that the composite (2) containing only 10% GaFn@MSN has only slight lower CFU but the composite (3) both GaFn@MSN and the ternary gallium fluoride chelate has significant lower CFU, which indicates the biofilm inhibition effect.

Figure 15:
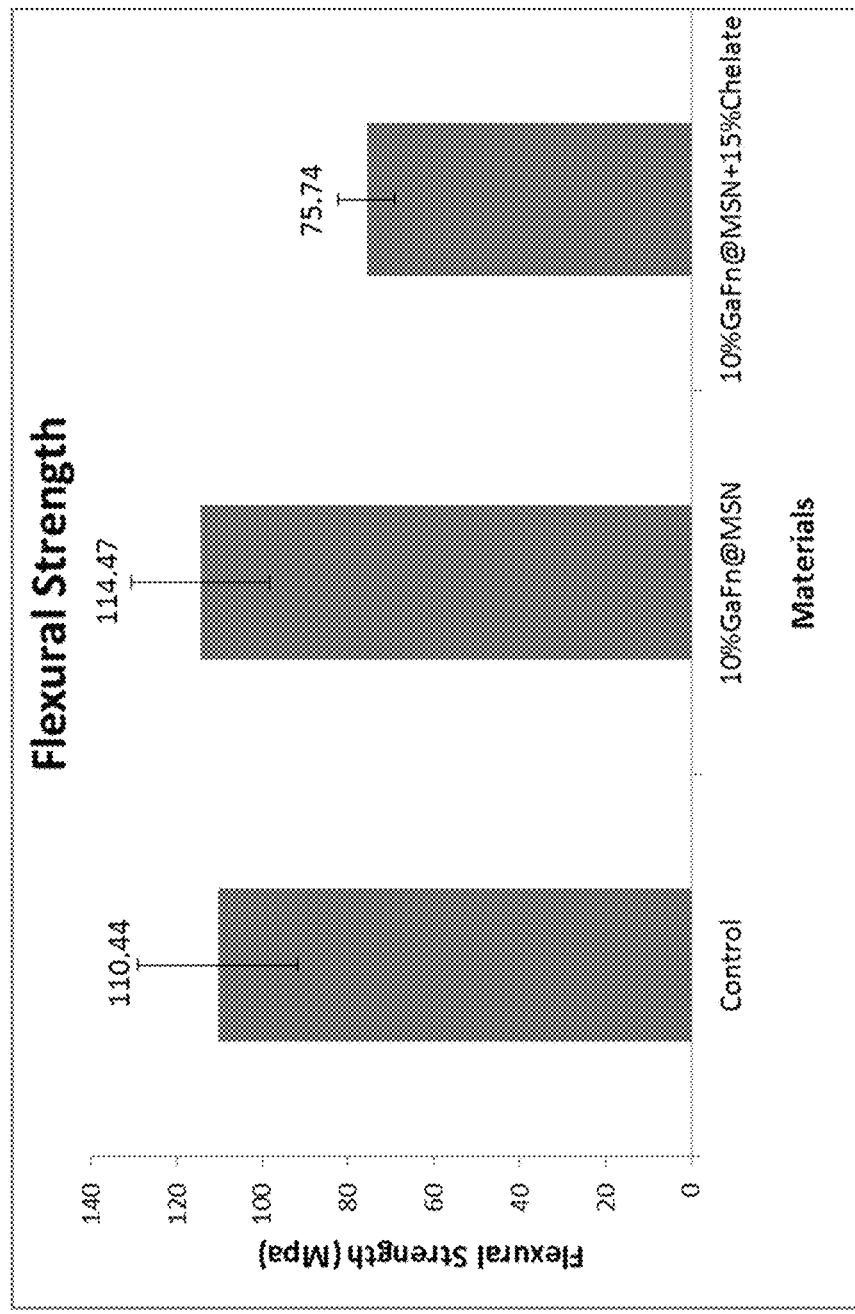
FIG. 15 shows flexural strength of composites.
Figure 16:
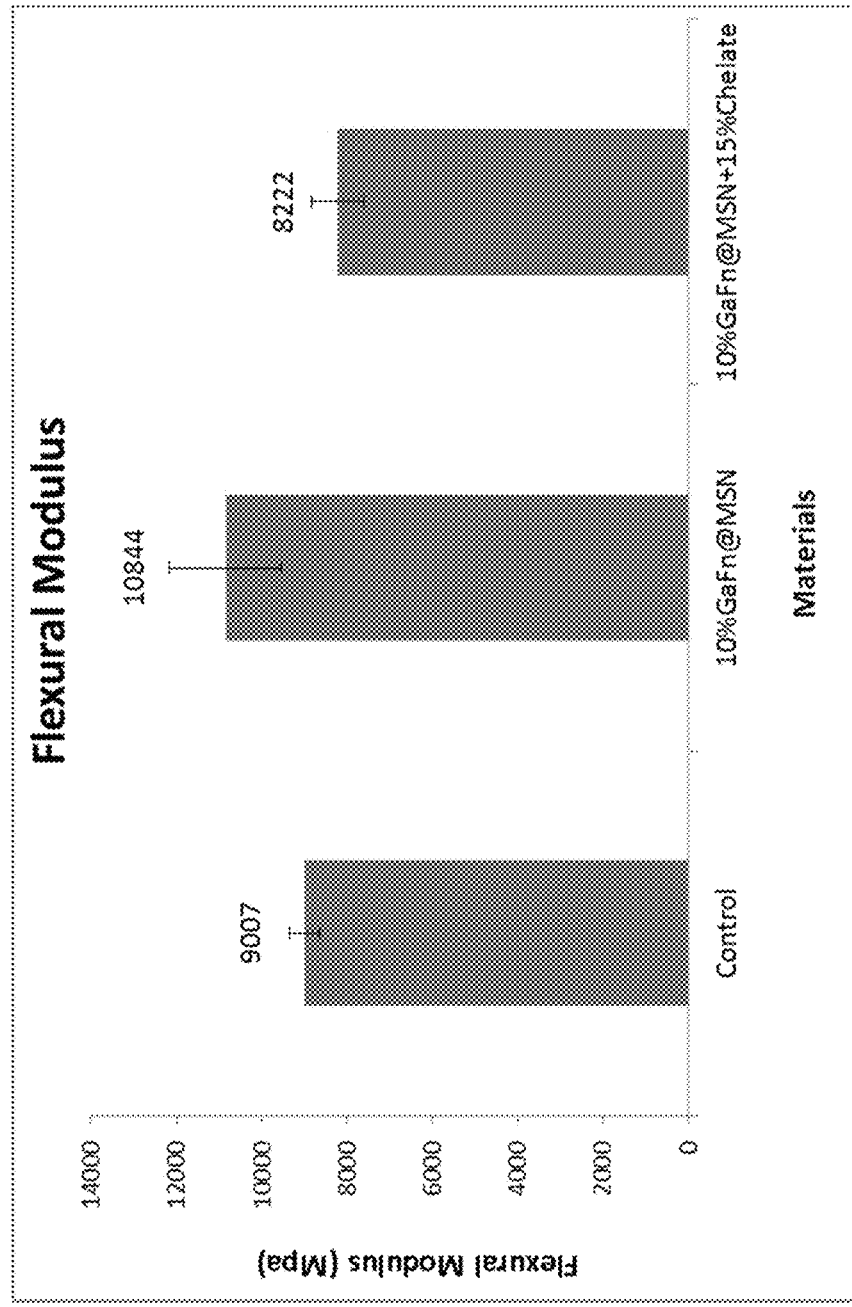
FIG. 16 shows flexural modulus of composites.

The mechanical properties (flexural strength and flexural modulus) of experimental composites were tested on Instron 5566 universal mechanical testing machine using three-point-bending method and crosshead speed of 1.0 mm/min. The results are shown in FIG. 15 and FIG. 16 respectively. In general the mechanical properties of the composite (2) are similar or higher than the control but the composite (3) containing ternary gallium fluoride chelate has significantly lower mechanical properties but its flexural strength (75.74 MPa) is very close to the requirement of ISO Standard 4049 (80 MPa).

In conclusion, these examples demonstrate that gallium can form new ternary fluoride chelates with chelating monomer. When such novel chelates are incorporated in dental composites and other resin-based dental materials, they can increase the release of gallium ions and enhance their inhibition effect against bacterial biofilm.

While the embodiments are described with reference to various implementations and exploitations, it will be understood that these embodiments are illustrative and that the scope of the invention is not limited to them. Many variations, modifications, additions, and improvements are also possible.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A gallium-releasing composition, comprising a filler according to Formula (1) and a monomer according to Formula (2):

$$M_mL_jGaX_n,\quad (1)$$

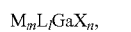
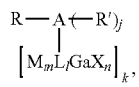

or a cured polymer thereof;
wherein, M is a positive ion of hydrogen, sodium, potassium, ammonium, or a quaternary ammonium;
wherein L is a chelating ligand; wherein X is an anion including hydroxide, nitrate, chloride, and fluoride;
wherein j is an integer from 0 to 4;
wherein l is an integer number from 1 to 3;
wherein m is an integer number from 0 to 6;
wherein n is an integer number from 0 to 6;
wherein k is an integer number from 1 to 3;

wherein, R is a substituted or unsubstituted aliphatic or aromatic group having 2 to 50 carbon atoms; and having at least one polymerizable group;
wherein, R' is a substituted or unsubstituted aliphatic or aromatic group having 2 to 50 carbon atoms, and having at least one polymerizable group;
wherein, A is a substituted or unsubstituted aliphatic or aromatic linkage group having 1 to 100 carbon atoms,
wherein Formula (1) is loaded on a nanoparticle or nanotube;
wherein the composition comprises 0.1% to 20% of the filler according to Formula (1); and
wherein the composition comprises 0.1% to 20% of the monomer of Formula (2).

2. The composition of claim 1, wherein L of Formula (1) is a chelating ligand comprising: oxalic acid, citric acid, phthalic acid, glutamic acid, tyrosine, serine, iminodiacetic acid, ethylenediiminodiacetic acid, nitrilotriacetic acid, catechol, acetylacetone, hexafluoroacetylacetone, benzoylacetone, N-(2- hydroxybenzyl)iminodiacetic acid, N-(2-hydroxyethyl)iminodiacetic acid, N-(2-aminoethyl) iminodiacetic acid, ethylendinitrilotetraacetic acid, diglycylethylenediaminetetraacetic acid, diethylenetrinitrilopentaacetic acid, salicylic acid, ethylenediiminodiacetic acid (EDDA), N,N-bis(carboxymethyl)aminoacetohydroxamic acid, ethylenediiminobis[(2-hydroxyphenyl)acetic acid] (EHPG), or diethylenetrinitrilopentaacetic acid (DTPA).

3. The composition of claim 1, wherein L of Formula (2) is one of the following chelating groups L2-L22 with dotted line indicating bonding location:

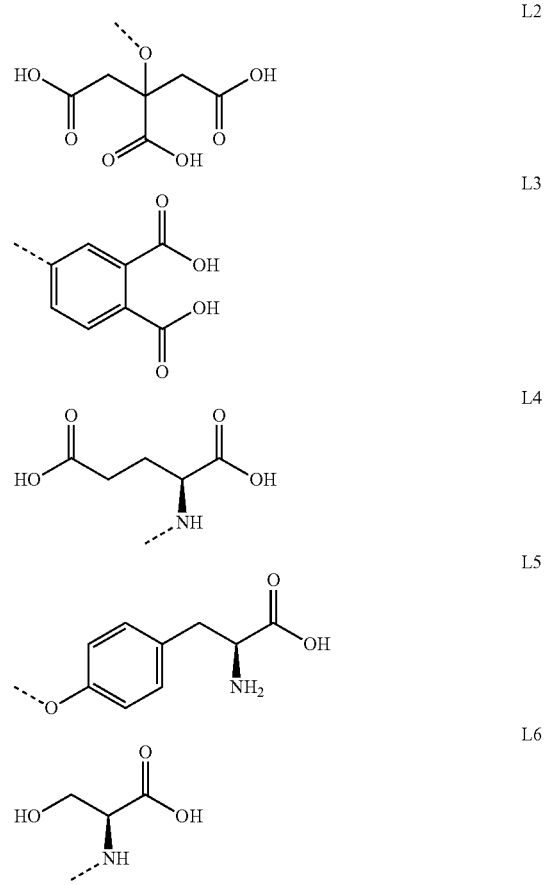

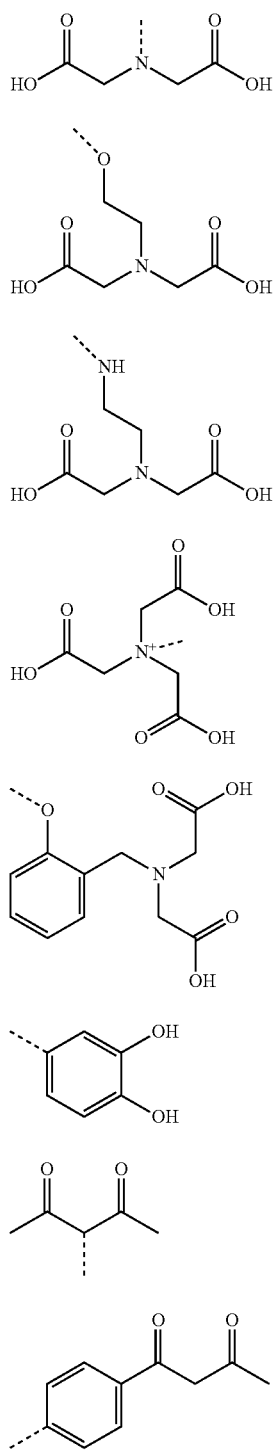
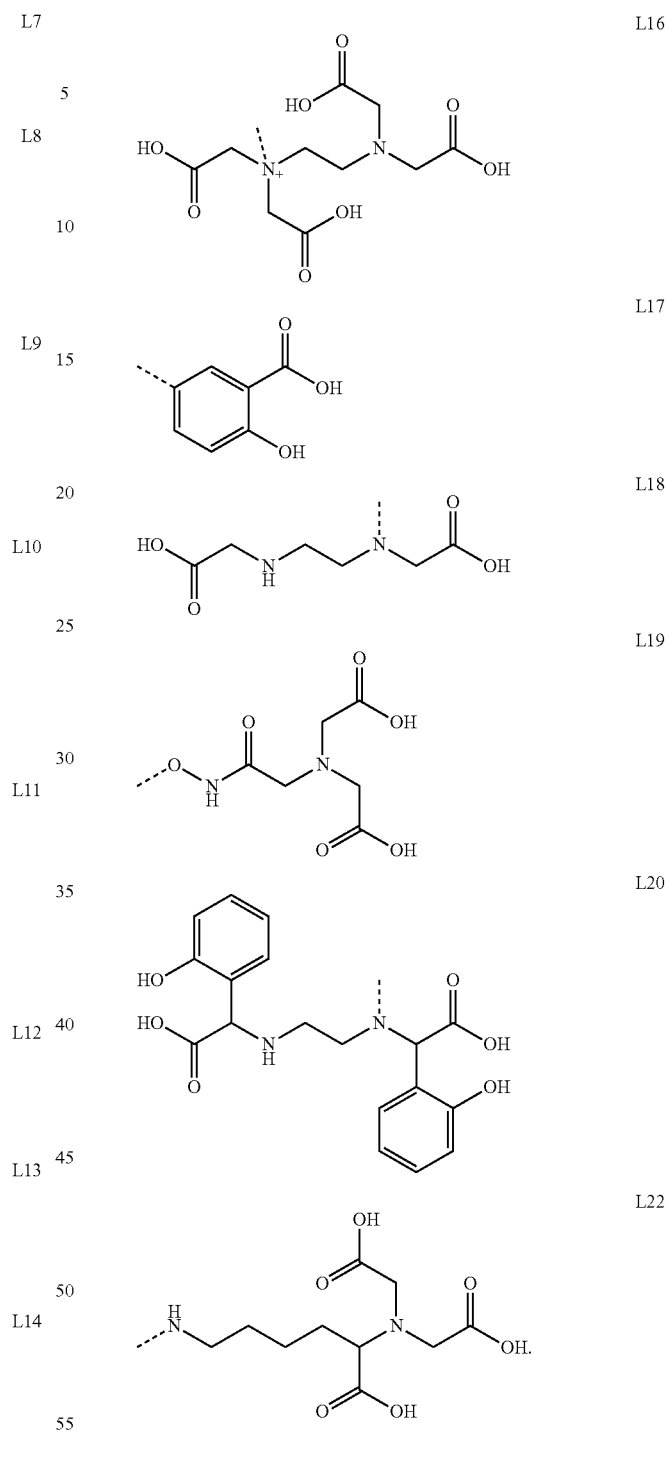
4. The composition of claim 1, wherein R and R' are one of R1-R6:
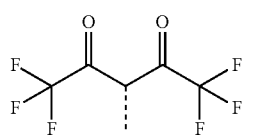

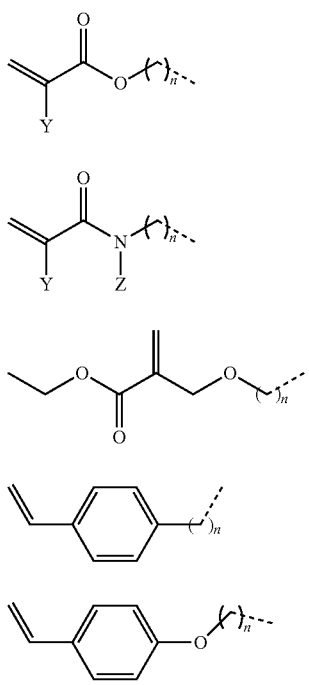

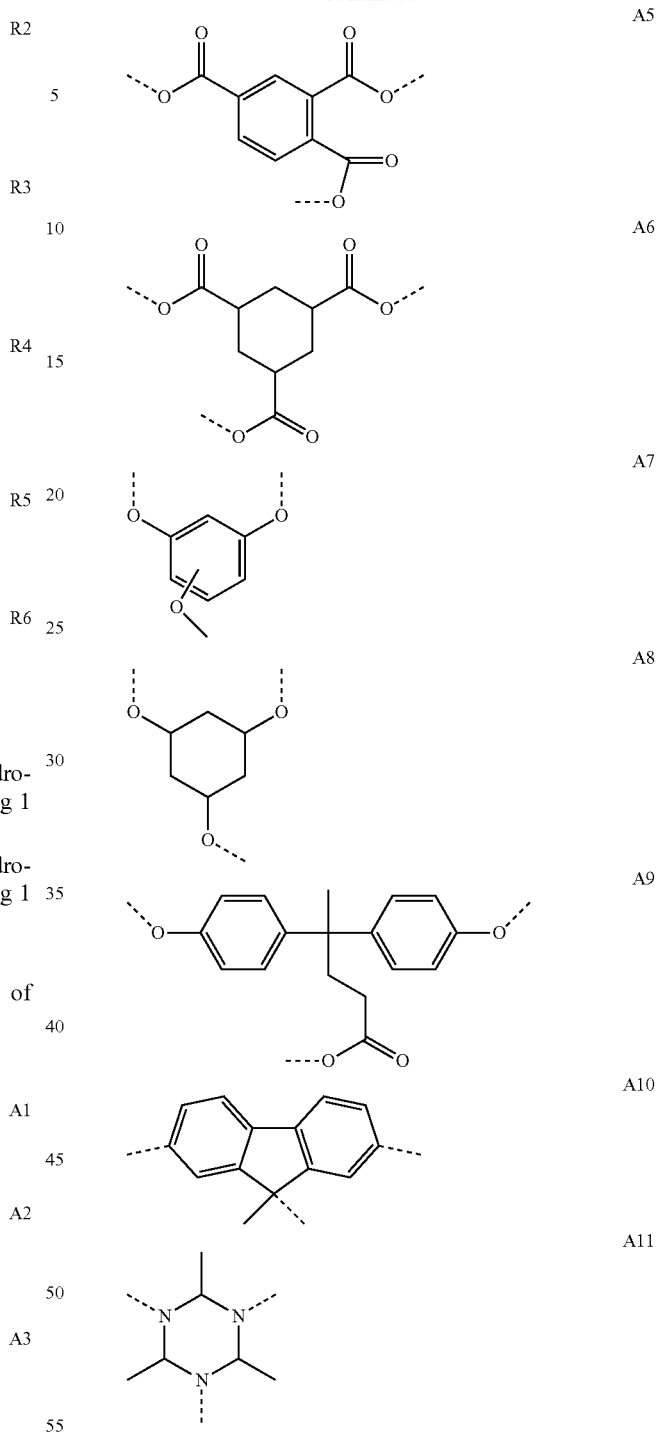

wherein Y is selected from the group consisting of hydrogen, and an unsubstituted aliphatic group containing 1 to 6 carbons;

wherein Z is selected from the group consisting of hydrogen, and an unsubstituted aliphatic group containing 1 to 6 carbons; and wherein n is a positive integer from 0 to 20.

5. The composition of claim 1, wherein A is one of A1-A11:

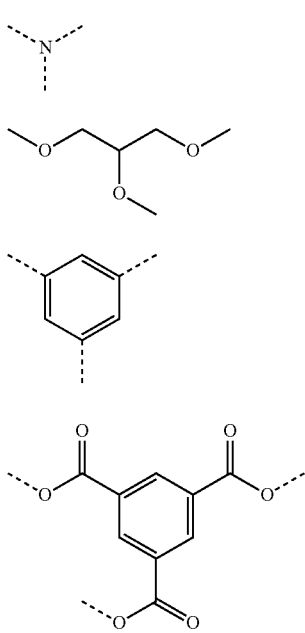

6. The composition according to claim 4, wherein Y is a methyl group and Z is hydrogen.

7. The composition according to claim 4, wherein Y is hydrogen and Z is one of methyl or ethyl group.

8. The composition of claim 1, wherein X is fluoride ion.

9. The composition of claim 1, wherein R and R' are the same.

10. The composition of claim 1, wherein the composition is a dental composite.

11. The composition of claim 1, wherein the composition is a denture based material.

12. The composition of claim 1, wherein the composition is a dental bonding agent.

13. The composition of claim 1, wherein the composition is a dental sealant.

14. The composition of claim 1, wherein the composition is a dental resin cement.

15. The composition of claim 1, wherein the composition is a resin-modified glass ionomer.

16. The composition of claim 1, wherein the composition is a dental varnish.

17. The composition of claim 1, wherein the composition is a mouth guard.

18. The composition of claim 1, wherein the composition is a medical device.

* * * * *

UNITED STATES PATENT AND TRADEMARK OFFICE
CERTIFICATE OF CORRECTION

PATENT NO. : 11,617,369 B2
APPLICATION NO. : 17/003765
DATED : April 4, 2023
INVENTOR(S) : Xiaoming Xu Page 1 of 1

It is certified that error appears in the above-identified patent and that said Letters Patent is hereby corrected as shown below:

In the Specification

At Column 1, Line numbers 13-16 change:
"This invention was made with government support under Grant No. R01DE026782 awarded by the National Institutes of Health. The government has certain rights in the invention."

To:
--This invention was made with government support under R01 DE026782 awarded by the National Institutes of Health. The government has certain rights in the invention.--

Signed and Sealed this
Twenty-fifth Day of November, 2025

John A. Squires
*Director of the United States Patent and Trademark Office*